(12) United States Patent
Ellinger et al.

(10) Patent No.: US 12,303,886 B2
(45) Date of Patent: May 20, 2025

(54) DEVICE FOR FRACTIONATING A SUSPENSION SAMPLE

(71) Applicant: BLINK AG, Jena (DE)

(72) Inventors: Thomas Ellinger, Jena (DE); Eugen Ermantraut, Jena (DE); Horst Bösneck, Jena (DE); Andreas Stärker, Jena (DE)

(73) Assignee: BLINK AG, Jena (DE)

( * ) Notice: Subject to any disclaimer, the term of this patent is extended or adjusted under 35 U.S.C. 154(b) by 1104 days.

(21) Appl. No.: 15/734,867

(22) PCT Filed: May 29, 2019

(86) PCT No.: PCT/EP2019/064056
§ 371 (c)(1),
(2) Date: Dec. 3, 2020

(87) PCT Pub. No.: WO2019/233871
PCT Pub. Date: Dec. 12, 2019

(65) Prior Publication Data
US 2021/0237051 A1 Aug. 5, 2021

(30) Foreign Application Priority Data
Jun. 6, 2018 (EP) ..................... 18176353

(51) Int. Cl.
| | |
|---|---|
| *B01L 3/00* | (2006.01) |
| *G01N 1/40* | (2006.01) |
| *G01N 33/49* | (2006.01) |

(52) U.S. Cl.
CPC .......... *B01L 3/5023* (2013.01); *G01N 1/4022* (2013.01); *G01N 1/405* (2013.01); *G01N 33/491* (2013.01); *B01L 2200/0631* (2013.01); *B01L 2300/0609* (2013.01); *B01L 2300/0681* (2013.01); *B01L 2300/0832* (2013.01)

(58) Field of Classification Search
CPC .......... B01L 3/5023; B01L 2200/0631; B01L 2300/0609; B01L 2300/0681; B01L 2300/0832; G01N 1/4022; G01N 1/405; G01N 33/491
See application file for complete search history.

(56) References Cited

U.S. PATENT DOCUMENTS

| | | |
|---|---|---|
| 5,496,741 A | 3/1996 | Pawliszyn |
| 6,825,046 B1 | 11/2004 | Forsyth |
| 2010/0226826 A1 | 9/2010 | Saul |
| 2011/0104027 A1 | 5/2011 | Pawliszyn |
| 2018/0021771 A1 | 1/2018 | Tamir |

FOREIGN PATENT DOCUMENTS

WO 2012031745 A1 3/2012

*Primary Examiner* — Brian J. Sines
(74) *Attorney, Agent, or Firm* — SALIWANCHIK, LLOYD & EISENSCHENK

(57) ABSTRACT

The present invention relates to a device for fractionating a suspension sample and to uses of such device. Furthermore, the present invention also relates to a method of fractionating a suspension sample into a liquid phase and a solid phase. The present invention also relates to a device and method for separating a sample comprising a solvent and two or more components having different molecular weights and being dissolved in said solvent, into said two or more components.

18 Claims, 11 Drawing Sheets principle of sample fractionation with LCST polymer body in container

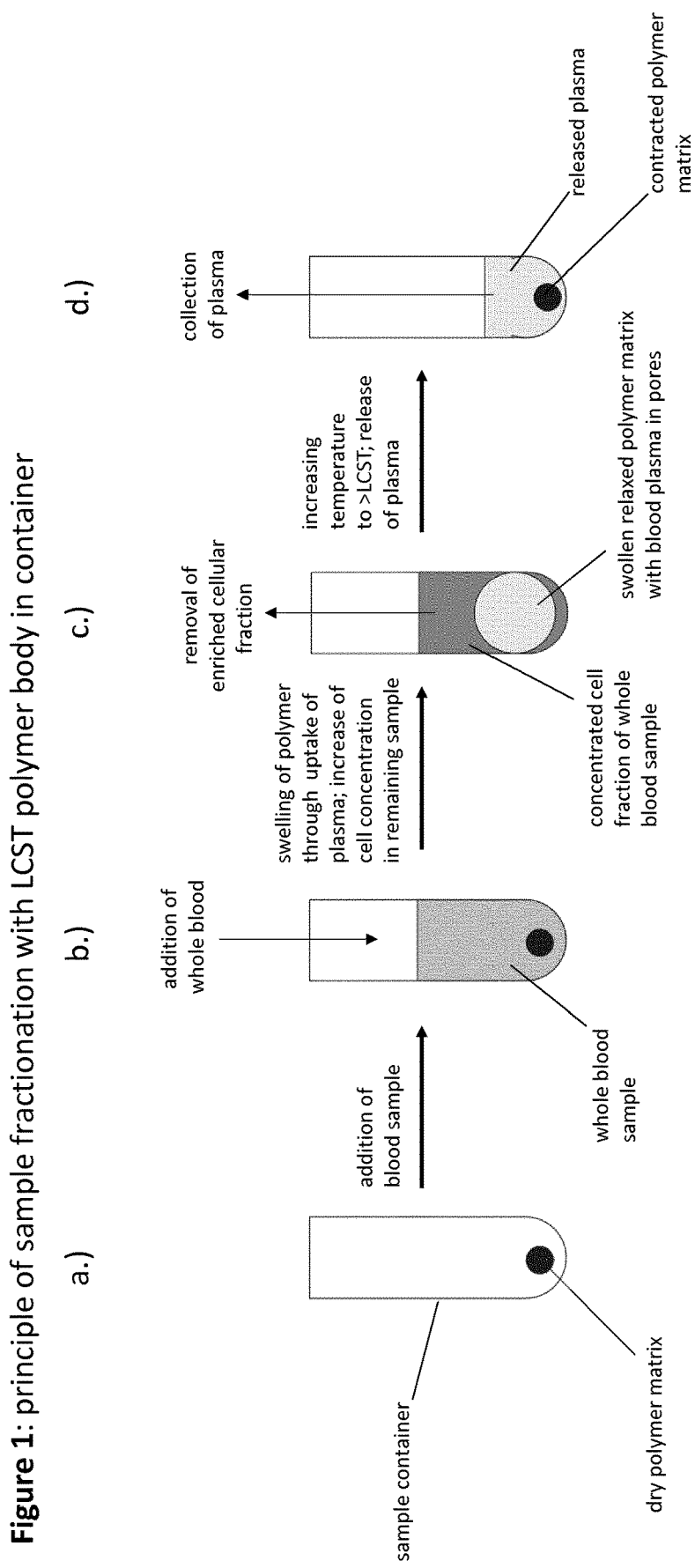

Figure 2: images showing collection of liquid from suspension sample
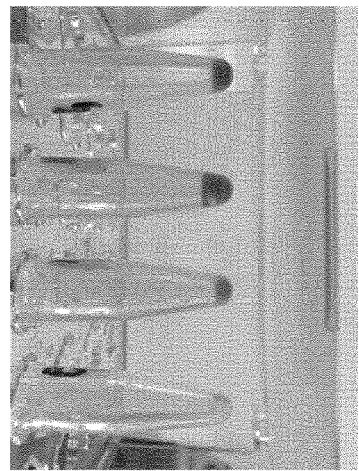
C)
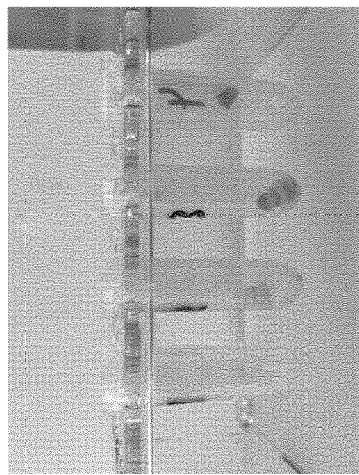
B)
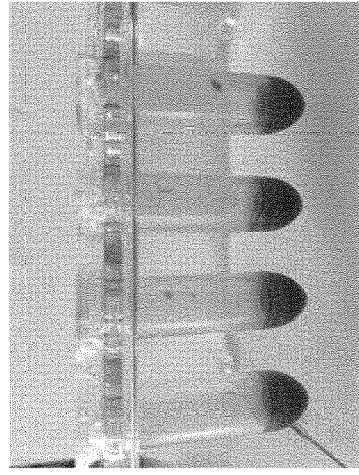
A)

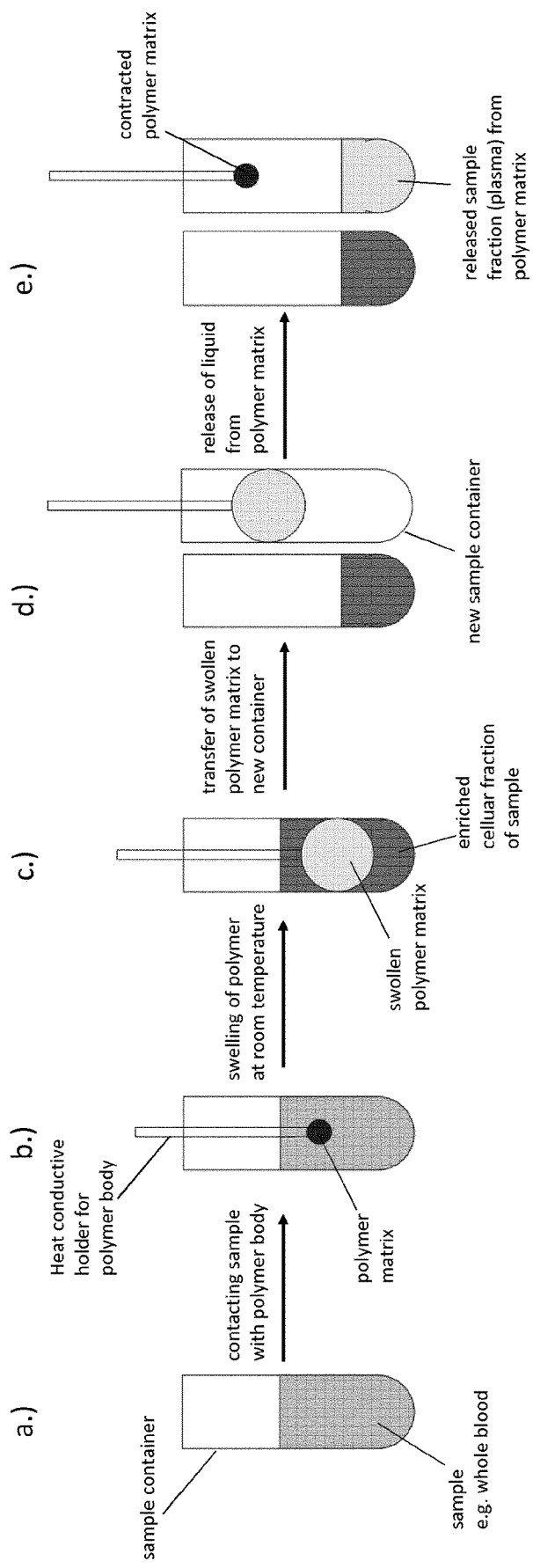

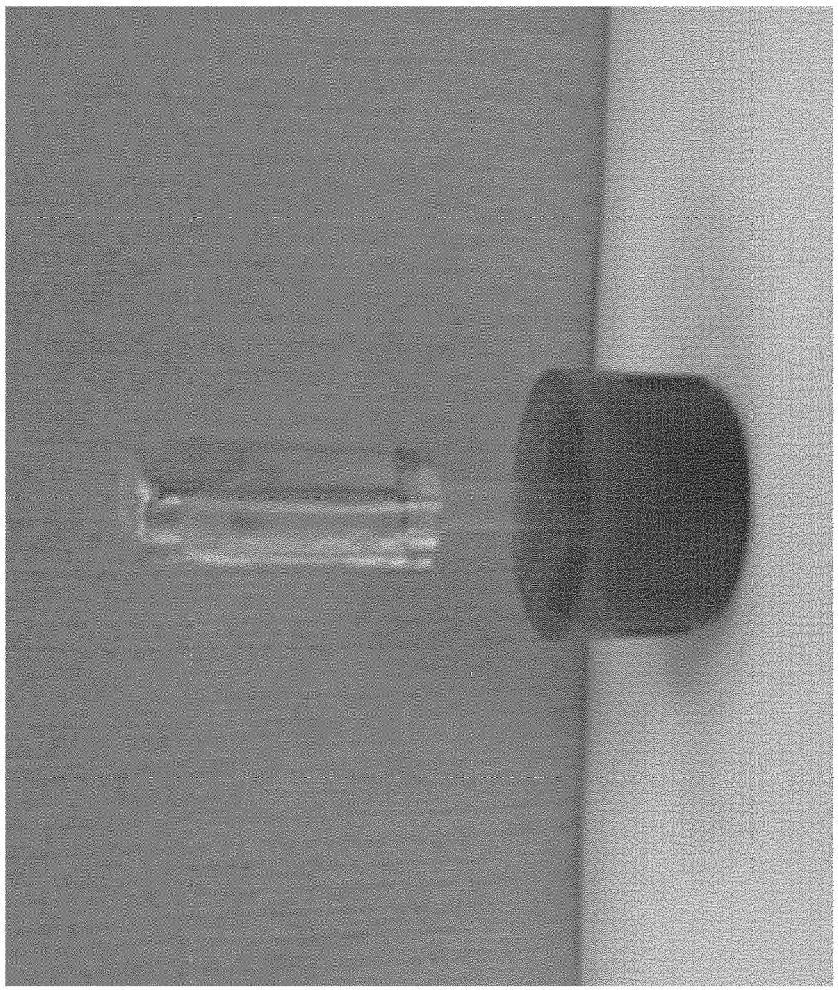
Figure 4: embodiment of a carrier tool with a polymeric matrix element immobilized on surface of carrier tool

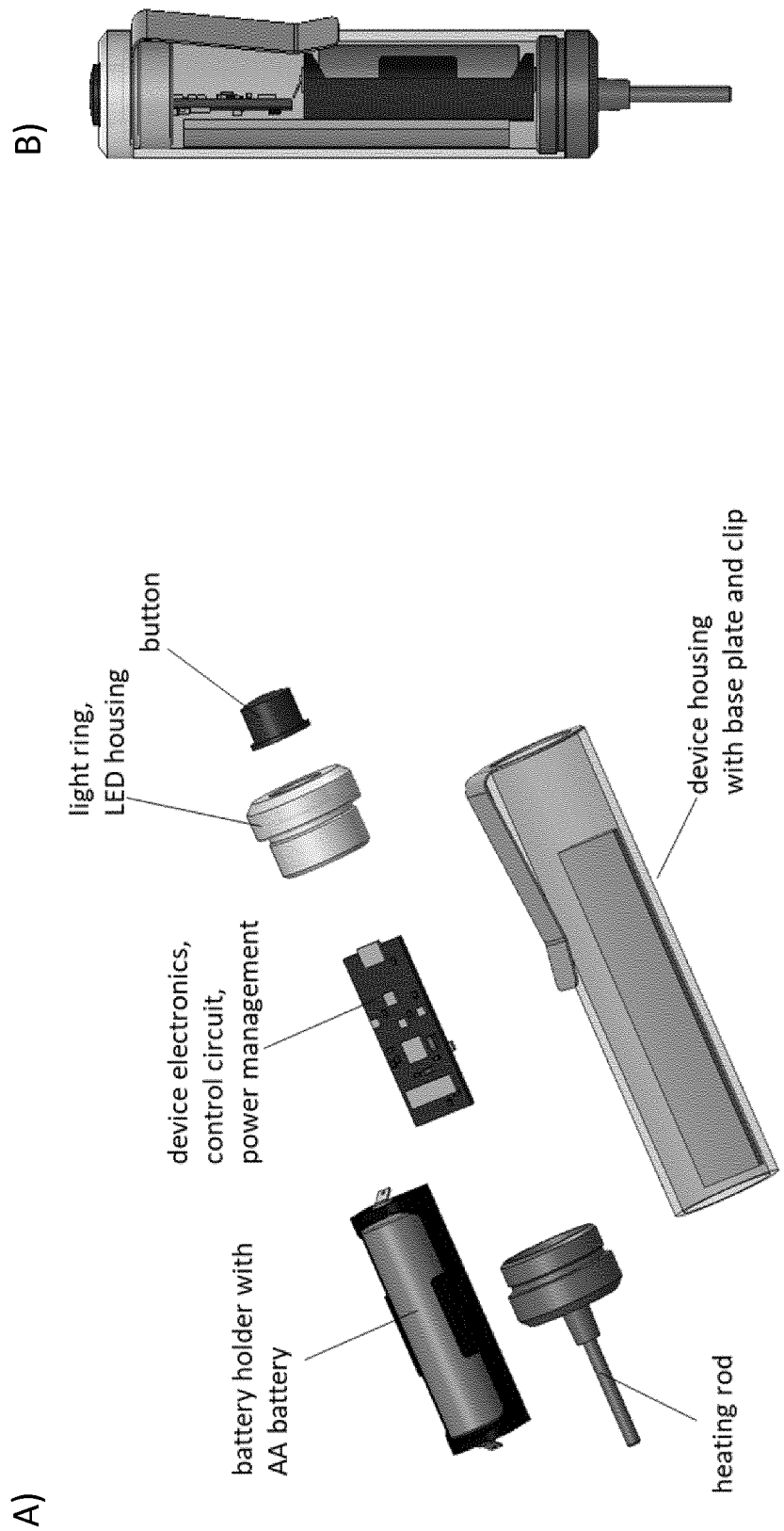
Figure 5: hand-held instrument, including heating and/or cooling means

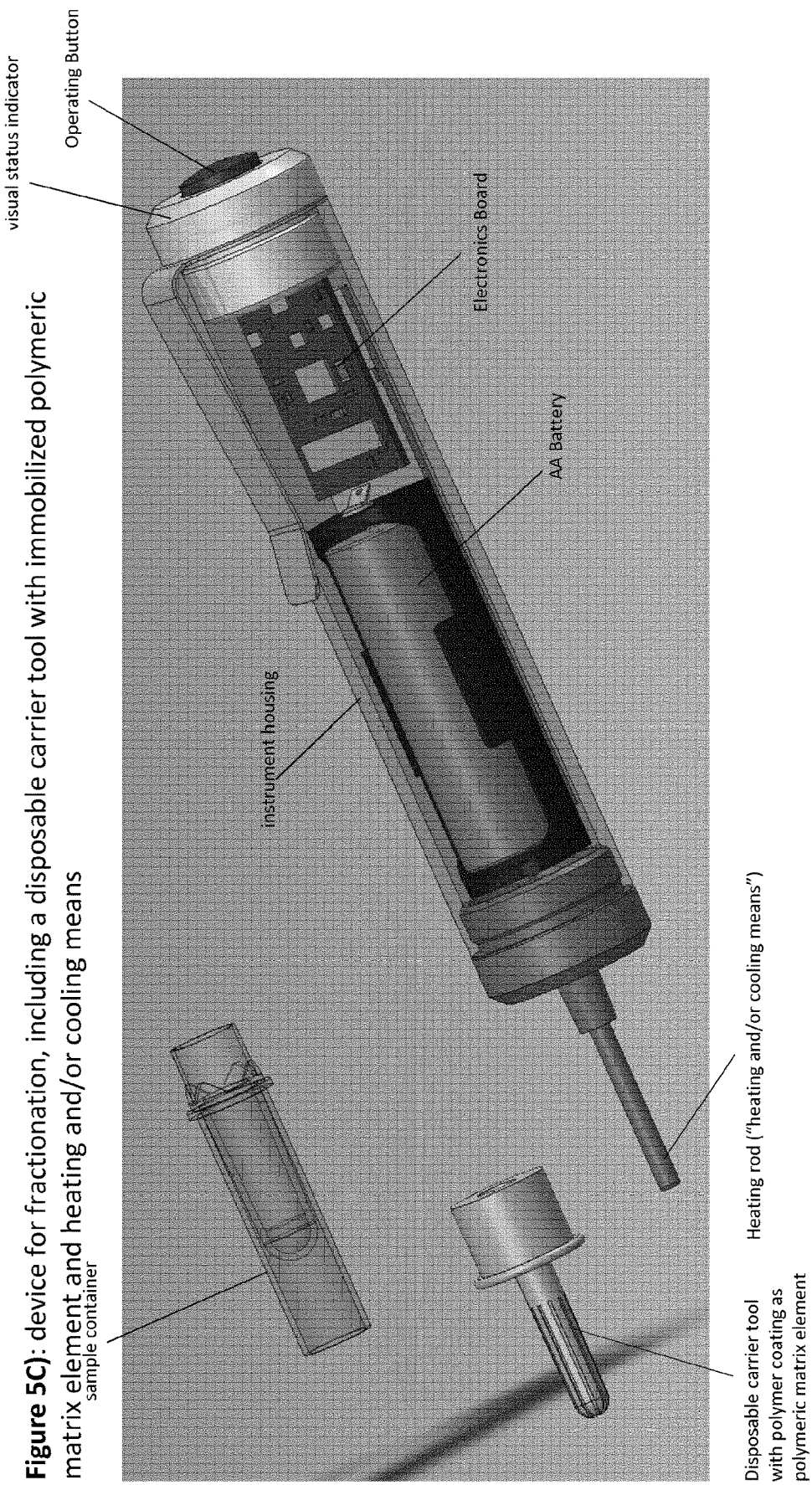
Figure 5C): device for fractionation, including a disposable carrier tool with immobilized polymeric matrix element and heating and/or cooling means

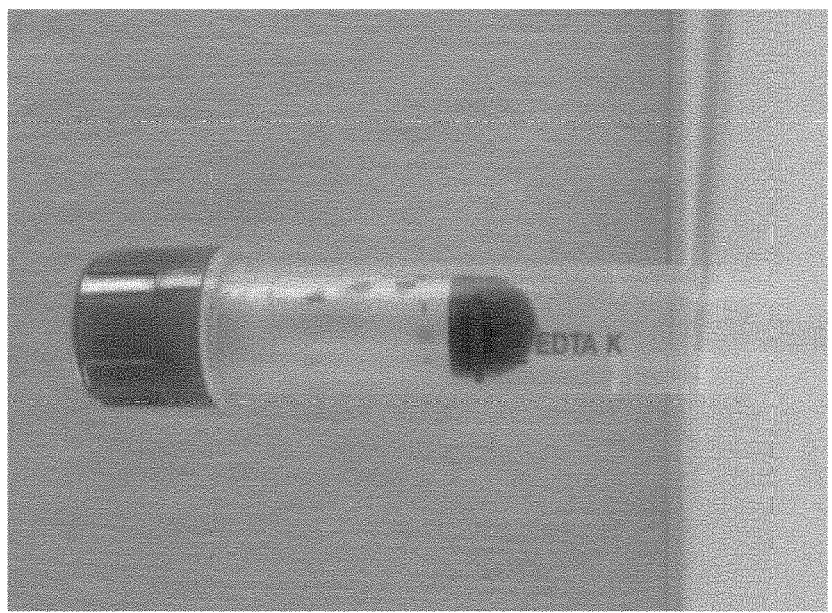
Figure 6:

Figure 6:
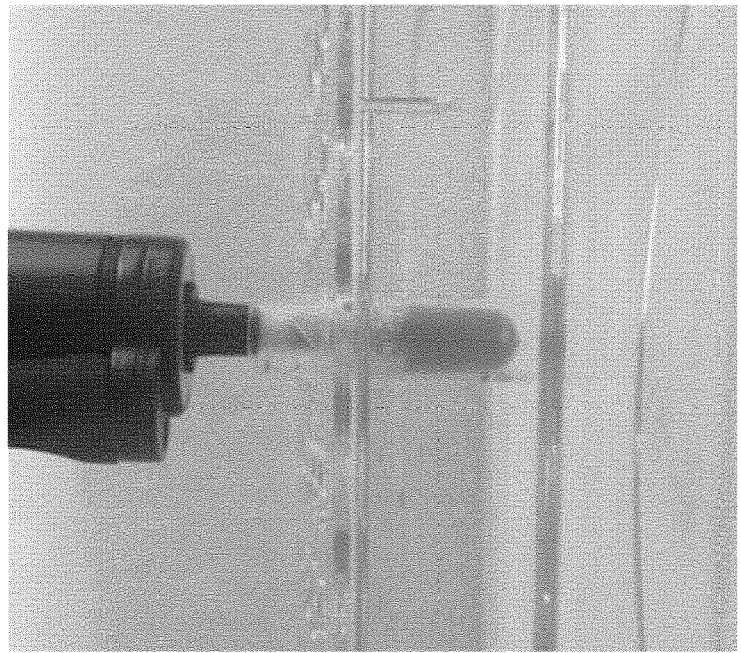
C)
D)

Figure 6:
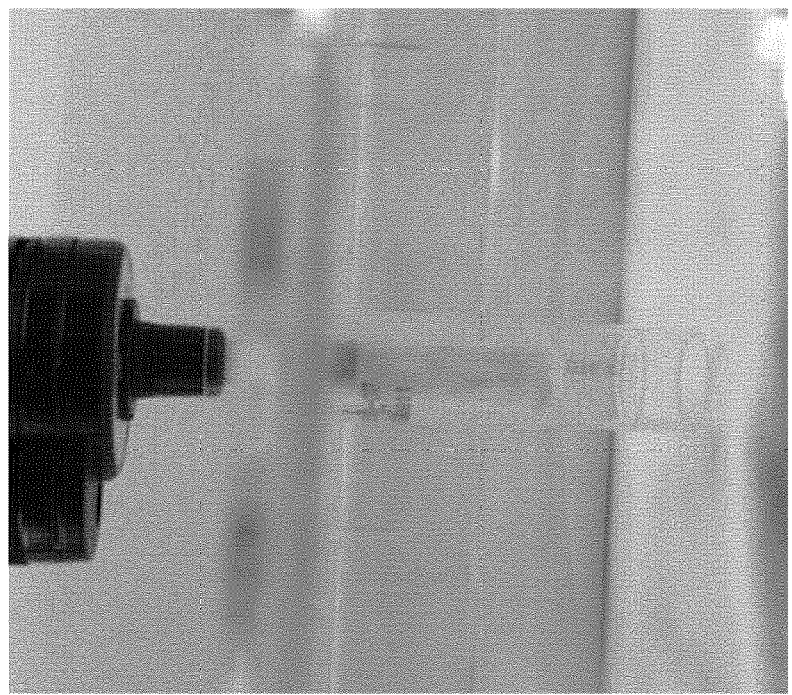
E)
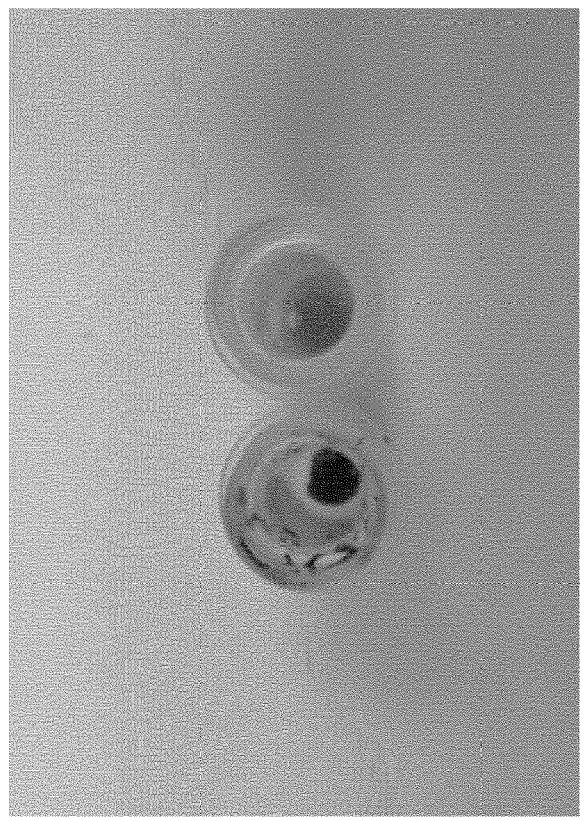
F)

DEVICE FOR FRACTIONATING A SUSPENSION SAMPLE

CROSS REFERENCE TO RELATED APPLICATIONS

This application is a National Stage Application of International Application Number PCT/EP2019/064056, filed May 29, 2019; which claims priority to European Application No. 18176353.3, filed Jun. 6, 2018.

The present invention relates to a device for fractionating a suspension sample and to uses of such device. Furthermore, the present invention also relates to a method of fractionating a suspension sample into a liquid phase and a solid phase. The present invention also relates to a device and method for separating a sample comprising a solvent and two or more components having different molecular weights and being dissolved in said solvent, into said two or more components.

The separation of suspension samples into different phases has been the subject of intense research and has been practiced over a long time. The clarification of beer or wine or the skimming of milk are typical examples.

Blood can be considered a good example of a particulate fraction suspended in an aqueous liquid. The fractionation of whole blood into a cellular and a plasma component constitutes an important step in many bio-analytical workflows. Typically this is achieved by centrifuging the sample in the corresponding sampling vessel. After separation of the cellular components from the liquid components by density in the centrifugal force field or by coagulation followed by centrifugation, the plasma or the serum is pipetted and further manipulated. During centrifugation, the sample vessel is moved about the rotational axis of the centrifuge. The effective centrifugal force causes an accelerated sedimentation and a solidification of the so-called blood clot or blood cake which is, effectively the cellular fraction of the blood. The solidity of such sedimented cellular fraction is decisive for the subsequent withdrawal of plasma or serum. Such withdrawal is done using a pipette with the centrifugal tube being in an upright position. A contact of the cellular fraction with the tip of the pipette which would cause a mixing of the two phases is to be avoided. This is the standard procedure in a laboratory but it requires the presence of a corresponding lab centrifuge and a qualified lab technician [1]. In a further variant of this methodology, there are sample tubes which are filled with a thixotropic gel which allows a separation of plasma and the cellular fraction [2]. However it is desirable to accomplish fractionation without centrifugation. Different filter based methods have been described in the literature. Typically a dedicated filter is used to hold back cellular components and to allow passage of the plasma liquid [3]. Because cells tend to block the filter, alternative approaches have been developed, such as sedimentation assisted filtration [4], sample dilution [5] or by employing a membrane filter or a hollow fiber membrane using tangential flow and a pump [6]. A blood sample is pumped through hollow fibers having asymmetrical pores. The plasma penetrates the hollow fiber wall and can be collected outside of the hollow fiber. Cells cannot permeate through the membrane and remain in the inside volume of the hollow fiber. Because of the tangential flow in relation to the membrane, a clogging of the membrane pores is avoided. By moving the sample back and forth through the hollow fibers, the cellular fraction is enriched and/or the plasma fraction can be separated. However, the method requires a considerable effort in terms of apparatuses used and is characterized by some significant dead volume(s) which limits its use to considerably large volumes of sample. Hence, small samples in the sub milliliter range cannot be processed efficiently using this technology. Different methods for plasma separation are based on the use of a soluble matrix that is placed in physical contact with a downstream surface of a filtration membrane. The soluble matrix is used to pull the sample passively through the membrane by a force generated through the dissolution process of the matrix in the plasma [7]. However this approach is only feasible if the matrix material does not interfere with the downstream analysis process. A similar approach represents the use of solid monoliths for filtering blood [8]. Typically in this approach, it is necessary to add some buffer in order to obtain sample of plasma from the device. The disadvantage of this method is that the obtained sample is diluted and modified by the buffer used.

Moreover, the process as generally all filter based approaches is not efficient with regard to the volume of plasma obtained. Microfluidic based tools have been also demonstrated to be suited for the purpose of plasma separation [9]. However, the need for complex microstructures and low plasma generation yield have prevented this technology to become widely applied.

Hence, there is a need for a simple tool for the separation/fractionation of a suspension sample into different phases, preferably a liquid phase and a solid phase.

There is also a need for a simple tool for separating a sample comprising a solvent and two components having different molecular weights and being dissolved in said solvent, into said two components.

There is furthermore a need for a tool for phase separation across a broad range of sample volumes. There is furthermore a need for a tool for phase separation of suspension samples which are in the micro-liter range, i.e. when only small volumes of sample, such as less than 1 ml, are available.

In a first aspect, the present invention relates to a device configured for separating a sample comprising a solvent and two components having different molecular weights and being dissolved in said solvent, into said two components, or for fractionating a suspension sample into a liquid phase and a solid phase, said device comprising at least one polymeric matrix element, said polymeric matrix element comprising a porous polymeric scaffold and an interstitial pore space within said polymeric scaffold, wherein said porous polymeric scaffold is composed of a polymer responsive to the change of at least one external condition to which said polymeric matrix element, during use of said device, is exposed, e.g. pH, temperature, salt conditions, presence or absence of chemicals. In one embodiment, said at least one polymeric matrix element has the capability of reversibly adopting, alternatively, an expanded and a contracted state, wherein reversible adaptation of an expanded state or contracted state occurs in response to the change of at least one external condition to which said polymeric matrix element, during use of said device, is exposed. Preferably, the at least one polymeric matrix element has the capability of repeatedly reversibly adopting such expanded and contracted state.

In one embodiment, the device further comprises at least one sample container, said at least one sample container containing, or being configured to contain, said at least one polymeric matrix element, said at least one sample container being capable of receiving a sample comprising a solvent and two components having different molecular weights and being dissolved in said solvent, or a suspension sample. The sample container, as used herein, is the container in which the sample to be separated into different components or to be fractionated, is provided or introduced, before separation or fractionation.

In one embodiment, said at least one polymeric matrix element is either a macroscopic solitary particle, preferably in the shape of a bead, a globe, a blob, a ball, a cube, a cuboid, a block, an ellipsoid, or an irregularly shaped body, or said at least one polymeric matrix element is a macroscopic body or layer immobilized on a surface of a substrate within said device.

In one embodiment, said at least one polymeric matrix element is detachable or removable from said device or configured to be detachable or removable, wherein preferably said at least one polymeric matrix element is a disposable single-use polymeric matrix element.

In one embodiment, said device further comprises means to effect a change of at least one external condition to which said polymeric matrix element, during use of said device, is exposed, wherein preferably said means to effect a change of at least one external condition are heating and/or cooling means.

In one embodiment, said means, preferably said heating and/or cooling means, are configured to expose said at least one polymeric matrix element to a change of at least one external condition, wherein preferably said means are part of said device and/or are integrated in said device and/or are configured to come into contact with said suspension sample or to become connected with said suspension sample.

In one embodiment, said device further comprises a carrier tool configured to allow the handling of said at least one polymeric matrix element, said carrier tool acting as a substrate having a surface on which said at least one polymeric matrix element is immobilized, said carrier tool being dimensioned such as to be able to be dipped into a sample comprising a solvent and two components having different molecular weights and being dissolved in said solvent, or into a suspension sample and such as to be able to bring said at least one polymeric matrix element into contact with said sample, preferably said suspension sample.

In one embodiment, said carrier tool is configured to be able to effect a change of at least one external condition to which said polymeric matrix element, during use of said device, is exposed, e.g. pH, temperature, salt conditions, presence or absence of chemicals, wherein, preferably, said carrier tool is configured to be able to effect a change of temperature.

In one embodiment, said carrier tool comprises heating and/or cooling means for heating and/or cooling said at least one polymeric matrix element, or said carrier tool is connected to or contacted with heating and/or cooling means for heating and/or cooling said at least one polymeric matrix element, wherein, preferably, said heating and/or cooling means are the heating and/or cooling means as defined above.

In one embodiment, said carrier tool is a disposable single-use carrier tool and is configured to be detachably connected to, detachably contacted with or to detachably comprise said heating and/or cooling means, wherein preferably said carrier tool is configured as a pen, a stick, a rod, a cylinder, a bar, a wand, a baton or a member, wherein said carrier tool has an interface to detachably connect to, detachably contact with or to detachably comprise said heating and/or cooling means.

In one embodiment, said device further comprises at least one liquid phase collection container, said at least one liquid phase collection container being configured to take up said polymeric matrix element and/or said carrier tool, if present, with said polymeric matrix element being immobilized on said carrier tool. It should be noted that such liquid phase collection container is a container that is different from said sample container. The liquid phase collection container typically is a container to which said polymeric matrix element, and/or said carrier tool, if present, with said polymeric matrix element being immobilized thereon, is transferred after the polymeric matrix element has been exposed to a suspension sample and after it has taken up a liquid phase from such suspension sample. Effectively, the liquid phase collection container serves the purpose of collecting a liquid phase that is expelled from the polymeric matrix element.

In one embodiment, said liquid phase collection container contains means for taking up a defined volume of said liquid phase and/or means for measuring a volume of said liquid phase.

It should be noted that, after the polymeric matrix element has taken up a liquid phase from a suspension sample, it may be that some parts of the solid phase from said suspension adhere or attach to said polymeric matrix element. It may therefore be necessary to remove such solid phase from the polymeric matrix element, preferably from the outside of the polymeric matrix element.

In one embodiment, for removal of said solid phase from said polymeric matrix element, especially if parts of said solid phase become attached or adhered to said polymeric matrix element, a) said sample container and/or said carrier tool, if present, and/or said liquid phase collection container, if present, comprise means to mechanically remove said solid phase from said polymeric matrix element, e.g. an orifice, a constriction, a slidable ring, a lip, an edge or an opening the inner dimensions of which match the outer dimensions of said polymeric matrix element; or b) said sample container and/or said carrier tool, if present, and/or said liquid phase collection container, if present, comprise a material having an affinity to said solid phase to which material said solid phase preferably adheres to, when being or getting in contact with it; or c) said sample container and/or said carrier tool, if present, and/or said liquid phase collection container, if present, comprise means to wash off said solid phase from said polymeric matrix element, such as a jet ejecting liquid to wash off said solid phase from said polymeric matrix element; or d) said device further comprises a separate tool to remove said solid phase from said polymeric matrix element, such as a spatula, a blade, a scraper In one embodiment, said device further comprises means for further processing and/or analyzing said liquid phase, wherein preferably said means for further processing and/or analyzing said liquid phase comprise a spectrophotometer and/or means to add one or several chemical agents to said liquid phase.

In one embodiment, said sample comprising a solvent and two components having different molecular weights and being dissolved in said solvent is an aqueous sample comprising a macromolecular component such as a protein or peptide or nucleic acid as one of the two components and a small molecule component, such as a dye or salt, as another of the two components. In one embodiment, said suspension sample is a whole blood sample, said liquid phase of said whole blood sample is blood plasma, and said solid phase of said whole blood sample is or comprises blood cells of said whole blood sample.

In one embodiment, said polymer responsive to the change of at least one external condition to which said polymeric matrix element, during use of said device, is exposed, is a thermoresponsive polymer which is either a thermoresponsive polymer having a lower critical solution temperature (LCST polymer), preferably selected from poly (N-isopropylacrylamide) (pNIPAM), poly(N-isopropylacrylamide/N,N'-Methylenebis(acrylamide), poly(N-isopropylacrylamide)-co-(acrylic acid), poly(N-isopropylacrylamide)-co-(acrylic acid)-co-(poly (ethyleneglycol) methyl ether acrylate, poly(N-isopropylacrylamide)-co-(poly(ethyleneglycol) diacrylate, poly(N-isopropylacrylamide)-co-(poly(ethyleneglycol) methyl ether acrylate, poly [2-(dimethylamino)ethyl methacrylate] (pDMAEMA), hydroxypropylcellulose, (P(VCL), and polyvinyl methyl ether, or said poly (vinylcaprolactame) thermoresponsive polymer is a thermoresponsive polymer having an upper critical solution temperature (UCST), preferably selected from poly (N-acryloyl glycinamide) (PNAGA), poly(allylamine)-co-poly (allylurea) and its derivatives, poly(methacrylamide), poly(N-acryloylaspargineamide), poly(N-methacryloylglutamineamide), poly (acrylamide)-co-(acrylonitrile). poly(sulfobetaine) s, poly (phosphorylcholine)s.

In one embodiment, said responsive polymer, in particular said thermoresponsive polymer, is crosslinked, preferably either by at least one crosslinking reagent bridging and interconnecting between different polymer chains within said polymer, or by the provision of a substrate within said device, in particular a substantially planar or curved substrate, adjacent to said polymeric matrix element, and by interfacial crosslinking of different polymer chains of said polymer to said substrate, in particular to a surface of said substrate.

In one embodiment, said at least one polymeric matrix element has the capability of reversibly, preferably repeatedly reversibly, adopting an expanded and a contracted state, and wherein, preferably, in the expanded state, the interstitial pore space has a volume which is at least 50%, preferably at least 60%, more preferably at least 70%, even more preferably at least 80% and even more preferably at least 90% of the total volume of said polymeric matrix element when said polymeric matrix element is in said expanded state.

In one embodiment, said interstitial pore space is not accessible to a solid phase of said suspension sample, but is accessible to a liquid phase of said suspension sample and is, preferably, dimensioned to accommodate at least more than 50% of said liquid phase of said suspension sample, more preferably more than 75%, even more preferably more than 90% of said liquid phase of said suspension sample.

In one embodiment, said interstitial pore space has pores the average diameter of which is <5 µm, preferably <3 µm, more preferably <1 µm.

In one embodiment, said device is dimensioned such as to fractionate a suspension sample having a volume in the range of from 10 µl to 500 µl, and wherein the interstitial pore space has a volume which takes up at least 50%, preferably at least 75%, more preferably at least 90% and even more preferably at least 95% of said suspension sample.

In one embodiment, said suspension sample has a volume of from 10 µl to 200 µl, preferably 50 µl to 200 µl, more preferably 100 µl to 200 µl.

In a further aspect, the present invention relates to a method of fractionating a suspension sample into a liquid phase and a solid phase, said method comprising the steps:
a) providing, in any order, but separately from each other, a device according to the present invention, as defined above, and a suspension sample, wherein said at least one polymeric matrix element of said device is in dry state, or wherein said at least one polymeric matrix element of said device is provided under conditions in which said responsive polymer is in a contracted state but wherein said at least one polymeric matrix element of said device is in a moist state;
b) exposing said at least one polymeric matrix element of said device to said suspension sample under an external condition allowing said polymeric matrix element to reversibly adopt an expanded state and thus allowing a liquid phase in said suspension sample to enter said interstitial pore space of said at least one polymeric matrix element, whilst excluding a solid phase in said suspension sample from said interstitial pore space;
c) removing said at least one polymeric matrix element from said sample, thereby removing said liquid phase contained within said interstitial pore space from said sample and thereby separating said liquid phase from a solid phase in said sample.

In one embodiment, in step c), said at least one polymeric matrix element is removed from a sample container, as defined further above, if present, and is transferred to a liquid phase collection container, as defined further above, if present.

In one embodiment, said method further comprises the step:
d) Changing an external condition to which said polymeric matrix element is exposed, to a condition allowing said polymeric matrix element to reversibly adopt a contracted state, thereby releasing said liquid phase from said polymeric matrix element.

In one embodiment, said polymer responsive to the change of at least one external condition is a thermoresponsive polymer, as defined further above, and said external condition is temperature.

In one embodiment, said suspension sample is a whole blood sample, said liquid phase of said whole blood sample is blood plasma, and said solid phase of said whole blood sample is or comprises blood cells of said whole blood sample, preferably the majority of all blood cells, more preferably all blood cells of said whole blood sample.

In a further aspect, the present invention also relates to the use of a device, as defined above, or of a polymer responsive to the change of at least one external condition, e.g. pH, temperature, salt conditions, presence or absence of chemicals, as defined above for fractionating a suspension sample into a liquid phase and a solid phase, preferably for fractionating a whole blood sample into blood plasma and blood cells, wherein preferably said use comprises the steps a)-c), as defined above, and optionally step d) as defined also above.

In a further aspect, the present invention relates to a method of separating a sample comprising a solvent and two components having different molecular weights and being dissolved in said solvent, into said two components, said method comprising the steps:
a) providing, in any order, but separately from each other, a device according to the present invention, as defined above, and a sample comprising a solvent and two components having different molecular weights and being dissolved in said solvent (hereafter in this embodiment: a "sample"), wherein said at least one polymeric matrix element of said device is in dry state, or wherein said at least one polymeric matrix element of said device is provided under conditions in which said responsive polymer is in a contracted state but wherein said at least one polymeric matrix element of said device is in a moist state;

b) exposing said at least one polymeric matrix element of said device to said sample under an external condition allowing said polymeric matrix element to reversibly adopt an expanded state and thus allowing a solvent (typically water or an aqueous solution) and a component dissolved in such solvent and having a low molecular weight (and thus a size small enough to fit into said pores), to enter said interstitial pore space of said at least one polymeric matrix element, whilst excluding the other component dissolved in such solvent and having a high molecular weight (and thus a size too big to fit into said pores) from said interstitial pore space;

c) removing said at least one polymeric matrix element from said sample, thereby removing said solvent and said low molecular weight component dissolved therein, contained within said interstitial pore space, from said sample and thereby separating said low molecular weight component dissolved in said solvent from a high molecular weight compound in said sample.

In one embodiment, in step c), said at least one polymeric matrix element is removed from a sample container, as defined further above, if present, and is transferred to a liquid phase collection container, as defined further above, if present.

In one embodiment, said method further comprises the step:

d) Changing an external condition to which said polymeric matrix element is exposed, to a condition allowing said polymeric matrix element to reversibly adopt a contracted state, thereby releasing said solvent and said low molecular weight component dissolved in said solvent, from said polymeric matrix element.

In one embodiment, said polymer responsive to the change of at least one external condition is a thermoresponsive polymer, as defined further above, and said external condition is temperature.

In one embodiment, said sample comprising a solvent and two components having different molecular weights and being dissolved in said solvent, is an aqueous solution of a biomolecule, such as a protein or nucleic acid, which additionally contains other dissolved components therein, such as a buffer, and/or salt(s), and/or low molecular weight components such as dyes etc. The sample may also be a preparation of large macromolecular biomolecule complexes, such as protein complexes, cell organelles, ribosomes, etc.

In a further aspect, the present invention also relates to the use of a device, as defined above, or of a polymer responsive to the change of at least one external condition, e.g. pH, temperature, salt conditions, presence or absence of chemicals, as defined above for separating a sample comprising a solvent and two components having different molecular weights and being dissolved in said solvent, as defined above, into said two components, wherein preferably said use comprises the steps a)-c), as defined above, and optionally step d) as defined also above.

The present inventors have devised a device that is configured for fractionating a suspension sample into a liquid phase and a solid phase, which device makes use of a polymer that is responsive to the change of at least one external condition to which the polymer is exposed.

The device may thus act as a filter which separates a solid phase from a liquid phase.

Likewise in certain embodiments, the device can also be used to separate two or more components that are dissolved in a solvent within a sample (and hence no longer can be distinguished by virtue of their different phase states ("solid" versus "liquid") and that only differ by their molecular weight, according to their different sizes. Hence the device according to such embodiments may act as a molecular sieve, and/or it may be used to enrich a dissolved component of a defined molecular weight, such as for example in dialysis. Hence the methodology of the present invention extends from a separation of solid particles (of a size for example in the μm-range) suspended in an aqueous medium from a liquid phase within such aqueous medium, to a size separation according to molecular weight of two components having different molecular weights and being dissolved in a liquid phase (with one of the components having a macromolecular weight, such as biomolecules, e.g. proteins, peptides, nucleic acids, biomolecule complexes, and thus being of a size in the nm-range or sub-nm-range, and the other dissolved component being a small molecule component such as a salt or buffer or other low molecular weight component such as a dye).

Hence embodiments according to the present invention relate to a filtering action which separates a solid phase from a liquid phase. Other embodiments relate to a molecular sieve action which separates two dissolved components according to their molecular weight.

In some embodiments aimed at a molecular sieve action, the separation that is achieved may not be complete, and in these embodiments, the devices and methods according to the present invention are for the purpose of enriching one of several, e.g. two, components, over the respective other components, wherein these components have different molecular weights and are (initially) dissolved in a sample comprising a solvent and two (or more) components (differing in their respective molecular weights).

The term "two components", as used herein should not be constructed to be limited to the presence of two components (of different molecular weights) only. Rather it is intended to also allow for the presence of further components having different molecular weights, which may also be separated using the devices and methods according to the present invention. In these instances with more than two components, the devices and methods according to the present invention may be employed repeatedly, using different polymeric matrix elements the interstitial pore spaces of which, in particular the pore sizes, will be adapted to the respective molecular weights of the components to be separated. The inventors envisage that the average pore size or average pore diameter of the respective polymeric matrix element defines a molecular weight boundary or molecular weight cut-off along which separation into different components will occur.

The polymer that is used in any of the embodiments according to the present invention is a polymer that is responsive to the change of at least one external condition to which the polymer is exposed. Typically, the "response" to the change of at least one external condition is a change in volume and/or phase of said polymer. Such polymer is herein also sometimes referred to as a "responsive polymer". More specifically, the device comprises at least one polymeric matrix element which comprises a porous polymeric scaffold and an interstitial pore space within the polymeric scaffold, wherein said porous polymeric scaffold is composed of a polymer that is responsive to the change of at least one external condition to which said polymeric matrix element, during use of the device, is exposed. Typical examples of such external conditions are pH, temperature, salt conditions, and/or the presence of absence of specific chemicals. In embodiments of the present invention, the polymeric matrix element of said device, or a plurality of such polymeric matrix elements, is (are) brought in contact with a suspension sample. Taking temperature as an example of an external condition, the polymeric matrix element is composed of a thermoresponsive polymer which exhibits a thermoresponsive phase change behavior upon reaching a critical temperature. In this case, such responsive polymer may be a thermoresponsive polymer, and may have a lower critical solution temperature (LCST) polymer or an upper critical solution temperature (UCST) polymer. If a lower critical solution temperature (LCST) polymer is below its lower critical solution temperature (LCST), the corresponding polymeric matrix element will be highly porous and will, upon heating of the polymeric matrix element above the LCST, contract. If, previously, the polymeric matrix element below the LCST was in an aqueous environment, the respective interstitial pore space within said polymeric matrix element will be filled with liquid, whereas upon heating and reaching and exceeding the lower critical solution temperature, the polymeric matrix element will contract and any liquid contained in the interstitial pore space will be expelled. Polymers that are responsive to the change of at least one external condition, such as thermoresponsive polymers have been studied and are known [10-12]. To the best knowledge of the inventors, the use of such responsive polymers for fractionating suspension samples has not been described before.

In one embodiment, the device according to the present invention further comprises at least one sample container which is intended to receive the suspension sample to be fractionated or the sample comprising a solvent and two components having different molecular weights and being dissolved in said solvent. The sample container contains or is configured to contain the at least one polymeric matrix element. It should be noted that a device according to the present invention may also comprise more than one polymeric matrix element, for example a plurality of polymeric matrix elements.

In one embodiment, the polymeric matrix element is a macroscopic solitary particle, such as a bead, a globe, a blob, a ball, a cube, a cuboid, a block, an ellipsoid, or an irregularly shaped body which preferably is dimensioned such that it can fit into the device and preferably into the sample container, if present. In another embodiment, the at least one polymeric matrix element is a macroscopic body, part or layer that is immobilized on a surface of a substrate within said device. In this embodiment, the surface of a substrate on which said polymeric matrix element is immobilized can be any suitable surface of a substrate located within said device. As an example, if the device comprises a sample container, part of the inner surface of said sample container may have said at least one polymeric matrix element immobilized thereon. Immobilization of said at least one polymeric matrix element on such surface occurs by known means, such as by appropriate covalent linkage/cross linking chemistry. The term "macroscopic particle" or "macroscopic body, part or layer" refers to a particle, body, part or layer that can be seen and observed using eye-sight and does not require specific optical means, such as a microscope, to observe such particle. The term "solitary" in this context refers to the fact that the particle has delimited boundaries and can be identified as a proper particle that is separate from its surroundings.

In one embodiment, said at least one polymeric matrix element is detachable or removable from said device. This is, because the polymeric matrix element serves to act as a reservoir volume into which the liquid phase of a suspension sample is taken up. Once the liquid phase or a liquid phase of a suspension sample has been taken up into said at least one polymeric matrix element, a separation from other phases of the suspension sample can be achieved easily by removal of the said at least one polymeric matrix element from the device. In many instances, once the polymeric matrix element has taken up a liquid phase from a suspension sample and has been removed from the device, and the liquid phase has been expelled from the polymeric matrix sample by an appropriate change of conditions, the polymeric matrix element has served its purpose and may be discarded. Hence, in preferred embodiments, said at least one polymeric matrix element is a disposable single use polymeric matrix element. This may be of particular relevance where the device is to be used for the separation/fractionation of suspension samples under sterile conditions.

In one embodiment, the device further comprises means to effect a change of at least one further external condition to which the polymeric matrix element, during use of the device, is exposed. Such means to effect a change of at least one external condition may take a plurality of different forms. For example it may be a reservoir of pH adjusting agent allowing the dosing of such pH adjusting agent to the suspension sample. In another embodiment it may be a reservoir containing a certain buffer, salt solution or other chemical, which reservoir allows the addition of defined amounts of such buffer, salt solution or other chemical to the suspension sample. In yet other embodiments, such means to effect a change of at least one external condition are heating and/or cooling means. Such heating and/or cooling means are particularly preferred when the responsive polymer is a thermoresponsive polymer. In one embodiment, such heating and/or cooling means may be or comprise a heater, for example in the form of a heating filament, alone or coupled with appropriate cooling means such as a fan or a tube through which a cooling liquid may flow. In another embodiment, said heating and/or cooling means may be one or several Peltier elements which may be operated in either heating or cooling mode. In yet another embodiment, the heating and/or cooling means may only comprise heating means, wherein cooling is achieved by convective heat transfer.

In one embodiment, the means to effect a change of at least one external condition, preferably the heating and/or cooling means, are configured to expose said at least polymeric matrix element to a change of at least one external condition. In one embodiment, said means, preferably said heating and/or cooling means, form part of the device for fractionating, or they are integrated in said device and/or they are configured to come into contact with said suspension sample or to become connected with said suspension sample. As one example, if said means are heating and/or cooling means and if said device comprises a container, said heating and/or cooling means may be formed as to surround said container and to thereby influence, control and modify, as necessary, the temperature of a suspension sample and of said at least one polymeric matrix element which will be in contact with the suspension sample.

In one embodiment, the device configured for fractionating a suspension sample further comprises a carrier tool that is configured to allow the handling of said at least one polymeric matrix element. Such carrier tool acts as a substrate having a surface on which said at least one polymeric matrix element may be immobilized. The carrier tool is dimensioned so as to be able to be dipped into a suspension sample and so as to bring the at least one polymeric matrix element into contact with said suspension sample. In this embodiment, the carrier tool serves the purpose of handling the at least one polymeric matrix element in an easy manner in that it allows to expose said at least one polymeric matrix element that is immobilized on said carrier tool to said suspension sample and, if necessary and desired, to also remove said at least one polymeric matrix element from said suspension sample. Such carrier tool may be configured in a plurality of ways. For example, it may be a rod, a stick etc. allowing the dipping of said polymeric matrix element into said suspension sample. Additionally, in a preferred embodiment, the carrier tool itself may be configured to be able to effect a change of at least one external condition to which the polymeric matrix element, during use of the device, is exposed. In a preferred embodiment, the carrier tool is configured to effect a change of temperature and preferably comprises heating and/or cooling means or is connected to or contacted with heating and/or cooling means which form part of the device. In a preferred embodiment, such heating and/or cooling means are the heating and/or cooling means as defined further above. In one embodiment, the carrier tool is a disposable, single-use carrier tool and is configured to be detachably connected to, detachably contacted with or to detachably comprise said heating and/or cooling means. It is preferred that the carrier tool is configured as a pen, a stick, a rod, a cylinder, a bar, a wand, a baton, or a member, wherein said carrier tool has an interface to detachably connect to, detachably contact with or to detachably comprise said heating and/or cooling means. In one specific embodiment, the carrier tool is configured as a hollow cylinder into which said heating and/or cooling means are inserted. In this embodiment, an operation of the heating and/or cooling means allows to change the temperature of the carrier tool and thus of any at least one polymeric matrix element immobilized thereon.

In one embodiment, said device further comprises at least one liquid phase collection container, said at least one liquid phase collection container being configured to take up said polymeric matrix element and/or said carrier tool, if present, with said polymeric matrix element being immobilized on said carrier tool.

In one embodiment, said liquid phase collection container serves as a reservoir and/or storage module for said liquid phase. In one embodiment, said liquid phase collection container is dimensioned such as to receive at least 50%, preferably at least 75%, more preferably at least 90% and even more preferably at least 95% of the liquid phase of said suspension sample. In one embodiment, the total volume of said liquid phase collection container does not exceed 5 ml, preferably 2 ml, more preferably 1 ml and even more preferably 0.5 ml.

In one embodiment, during use of said device, said polymeric matrix element and/or said carrier tool, if present, with said polymeric matrix element immobilized thereon, is transferred to said liquid phase collection container from said sample container after said polymeric matrix element has been in contact with a suspension sample under conditions allowing said polymeric matrix element to take up at least part of said liquid phase of said suspension sample. In such an embodiment it is preferred that after transferring said polymeric matrix element containing said liquid phase to said liquid phase collection container, conditions are applied under which at least part of said liquid phase contained in said polymeric matrix element is released from said polymeric matrix element to said liquid phase collection container.

In one embodiment said liquid phase collection container serves a reservoir and/or storage device for said liquid phase.

In one embodiment, said device for fractionating a suspension sample further comprises means for further processing and/or analyzing said liquid phase, wherein preferably said means for further processing and/or analyzing said liquid phase comprise a spectrophotometer and/or means to add chemical agents to said liquid phase. Such chemical agents may be used to further modify said liquid phase. For example, a spectrophotometer may be used to detect the presence or absence of one or several analytes, and for such detection the addition of chemical reagents may be necessary in order to enable such detection. For example, such chemical reagents may be one or several dyes, chromophores, antibodies, or other suitable detection agents In one embodiment, said liquid phase collection container contains means for taking up a defined volume of said liquid phase and/or means for measuring a volume of said liquid phase of said suspension sample.

In one embodiment, a) said sample container and/or said carrier tool, if present, and/or said liquid phase collection container, if present, comprise means to mechanically remove said solid phase from said polymeric matrix element, e.g. an orifice, a constriction, a slidable ring, a lip, an edge or an opening the inner dimensions of which match the outer dimensions of said polymeric matrix element; or b) said sample container and/or said carrier tool, if present, and/or said liquid phase collection container, if present, comprise a material having an affinity to said solid phase to which material said solid phase preferably adheres to, when being or getting in contact with it; or c) said sample container and/or said carrier tool, if present, and/or said liquid phase collection container, if present, comprise means to wash off said solid phase from said polymeric matrix element, such as a jet ejecting liquid to wash off said solid phase from said polymeric matrix element; or d) wherein said device further comprises a separate tool to remove said solid phase from said polymeric matrix element, such as a spatula, a blade, a scraper.

The device according to the present invention is particularly useful in the context of a fractionation of whole blood into plasma and blood cells as the liquid phase and solid phase, respectively. Hence, in one embodiment, the suspension sample is a whole blood sample, and the device is configured for fractionating whole blood into blood plasma and a solid phase comprising blood cells. In one embodiment, the plasma is platelet-enriched. In another embodiment, the blood plasma is devoid of platelets. In one embodiment, the polymer responsive to the change of at least one external condition to which said polymeric matrix element is exposed, is a thermoresponsive polymer. Such thermoresponsive polymer is either a thermoresponsive polymer having a lower critical solution temperature (LCST), or is a thermoresponsive polymer having an upper critical solution temperature (UCST). The term "thermoresponsive polymer" refers to a polymer the physical qualities of which, in particular, its affinity to water, are dependent on the external temperature to which the polymer is exposed. In one embodiment, a thermoresponsive polymer in accordance with the present invention exhibits a change of affinity to water with temperature. For example, a thermoresponsive polymer that has a lower critical solution temperature (LCST) is in a hydrated expanded state at temperatures below such LCST. At temperatures above the LCST, the polymer is in a contracted non-hydrated state. By cycling the at least one polymeric matrix element between the two states, it is possible to repeatedly (if desired) and reversibly accommodate liquid in the polymeric matrix element and thereafter expel it again from the polymeric matrix element, if and when desired. If such liquid is taken up into the polymeric matrix element, into the interstitial pore space within said polymeric matrix element, the solid particles in said suspension sample will remain outside of such polymeric matrix element. Thus, a separation of a liquid phase within said polymeric matrix element and a solid phase outside of said polymeric matrix element is achieved. When the polymeric matrix element is in an expanded state, the solvent/liquid has access to all or substantially all of the pores or a defined fraction of the pores, whereas the solid phase, such as blood cells, do not have access thereto. In such a swollen state, the polymeric matrix element may be removed from the blood cells and separated therefrom, thus achieving a fractionation into different phases.

In one embodiment, the responsive polymer, in particular the thermoresponsive polymer, is crosslinked, preferably either by at least one crosslinking reagent bridging and interconnecting between different polymer chains within said polymer, or by the provision of a substrate within said device, in particular a substantially planar or curved substrate, adjacent to said polymeric matrix element, and by interfacial crosslinking of different polymer chains of said polymer to said substrate, in particular to a surface of said substrate. In one embodiment, especially in this context, the surface of a substrate on which said responsive polymer is crosslinked (or immobilized) is a surface of said at least one sample container, if present, or is a surface of said carrier tool, if present.

In embodiments according to the present invention, said at least one polymeric matrix element, due to the presence of said responsive polymer, has the capability of reversibly adopting an expanded and a contracted state. Preferably, in the expanded state, the interstitial pore space has a volume which is at least 50%, preferably at least 60%, more preferably at least 70%, even more preferably at least 80% and even more preferably at least 90% of the total volume of said polymeric matrix element, when said polymeric matrix element is in the expanded state.

Furthermore, in one embodiment, the interstitial pore space is not accessible to a solid phase of the suspension sample, but is accessible to a liquid phase of the suspension sample. Taking whole blood as an example, the interstitial pore space is accessible to the plasma within said blood, but is not accessible to the blood cells, preferably to the red and white blood cells. The interstitial pore space may be accessible to blood platelets, depending on whether platelet-rich plasma is desired or not. The interstitial pore space can be adjusted appropriately to have pores, the average diameter of which allows for an exclusion of the desired solid phase and an inclusion/uptake into the interstitial pore space of the desired liquid phase. For example, in one embodiment, the interstitial pore space may have pores the average diameter of which is <5 μm, preferably <3 μm, more preferably <1 μm. When the device is used for effecting a size separation of two dissolved components which differ from each other by their respective molecular weights and/or for enriching one of these two components, the interstitial pore space may have pores the average diameter of which is well below the μm-range, e.g. 0.1 nm to 500 nm, preferably 1 nm to 100 nm. The size of the pores is chosen such as to suit the intended purpose of the device.

In one embodiment, the interstitial pore space is not accessible to a solid phase of the suspension sample, but is accessible to a liquid phase of the suspension sample. Preferably, the interstitial pore space is dimensioned to accommodate at least more than 50% of the liquid phase of said suspension sample, more preferably more than 75%, even more preferably more than 90% of said liquid phase of said suspension sample.

In one embodiment, the device is particularly suited and configured for fractionating suspension samples which have volumes <1 ml. In one embodiment, the device according to the present invention is dimensioned such as to fractionate a suspension sample having a volume in the range of from 10 μl to 500 μl, and the interstitial pore space of said at least one polymeric matrix element of said device has a volume which takes up at least 50%, preferably at least 75%, more preferably at least 90% and even more preferably at least 95% of said suspension sample. Hence, in one embodiment, the interstitial pore space of said polymeric matrix element has a volume which is at least 50% of the suspension sample volume of 10 μl to 500 μl, i.e. the volume of said interstitial pore space is at least 5 μl to at least 200 to 250 μl; preferably the interstitial pore space has a volume which is at least 75% of the suspension sample volume of 10 μl to 500 μl, i.e. the interstitial pore space has a volume which is at least 7.5 μl to at least 375 μl; more preferably the interstitial pore space has a volume which is at least 90% of the suspension sample volume of 10 μl to 500 μl, i.e. the interstitial pore space has a volume which is at least 9 μl to at least 450 μl; and even more preferably the interstitial pore space has a volume which is at least 95% of the suspension sample volume of 10 μl to 500 μl, i.e. the interstitial pore space has a volume which is at least 9.5 μl to at least 475 μl. In this context, in one embodiment, the total volume of the interstitial pore space of said polymeric matrix element does not exceed the volume of said suspension sample. Hence, as an example, if the volume of the suspension sample is 500 μl, the volume of said interstitial pore space is preferably not greater than 500 μl. In one embodiment, the volume of said interstitial pore space is 250 μl or 375 μl or 450 μl or 475 μl. As another exemplary embodiment, where the suspension sample has a volume in the range of from 10 μl to 200 μl, the volume of said interstitial pore space is in the range of from 5 μl to 200 μl. In another embodiment, where the suspension sample has a volume from 50 μl to 200 μl, the volume of said interstitial pore space is in the range of from 25 μl to 200 μl. In yet another embodiment, where the suspension sample has a volume in the range of from 100 μl to 200 μl, the volume of said interstitial pore space is in the range of from 50 μl to 200 μl.

In a further aspect, the present invention also relates to a method of fractionating a suspension sample into a liquid phase and a solid phase, wherein the method comprises the steps:

a) providing, in any order, but separately from each other, a device according to the present invention as defined above, and a suspension sample, wherein said at least one polymeric matrix element of said device is in a dry state or wherein said at least one polymeric matrix element of said device is provided under conditions in which said responsive polymer is in a contracted state but wherein said at least one polymeric matrix element of said device is in a moist state;

b) exposing said at least one polymeric matrix element of said device to said suspension sample under an external condition allowing said polymeric matrix element to reversibly adopt an expanded state thus allowing a liquid phase in said suspension sample to enter said interstitial pore space of said at least one polymeric matrix element, whilst excluding a solid phase in said suspension sample from said interstitial pore space;

c) removing said at least one polymeric matrix element from said sample, thereby removing said liquid phase contained within said interstitial pore space from said sample and thereby separating said liquid phase from a solid phase in said sample.

In one embodiment, during use of said device in said method of fractionating, in step c), said polymeric matrix element and/or said carrier tool, if present, with said polymeric matrix element immobilized thereon, is transferred to said liquid phase collection container from said sample container after said polymeric matrix element has been in contact with a suspension sample under conditions allowing said polymeric matrix element to take up at least part of said liquid phase of said suspension sample. In such an embodiment it is preferred that after transferring said polymeric matrix element containing said liquid phase to said liquid phase collection container, conditions are applied under which at least part of said liquid phase contained in said polymeric matrix element is released from said polymeric matrix element to said liquid phase collection container.

In one embodiment said liquid phase collection container serves a reservoir and/or storage device for said liquid phase.

In one embodiment of the method, the method may further comprise the step:

d) changing an external condition to which said polymeric matrix element is exposed to a condition allowing said polymeric matrix element to reversibly adopt a contracted state, thereby releasing said liquid phase from said polymeric matrix element.

It should be noted that in certain embodiments of the method according to the present invention, in step a), the device according to the present invention (and thus the polymeric matrix element comprised within said device) may, instead of being dry, be provided in a wet, but contracted state, i.e. the polymeric matrix element is not in a dry state but is provided under external conditions in which the responsive polymer is in a contracted state, but may be moist, for example there may be a certain amount of buffer (or other liquid) or a layer of buffer (or other liquid) covering said polymeric matrix element. In this embodiment, subsequently in step b), the at least one polymeric matrix element is exposed to said suspension sample under external conditions which allow the polymeric matrix element to reversibly adopt an expanded state and thus allowing a liquid phase in said suspension sample to enter the interstitial pore space of said at least one polymeric matrix element (as in the embodiment, where the polymeric matrix element is provided in a dry state). The subsequent step c) and the subsequent optional step d) are as defined before.

In a preferred embodiment according to the present invention, the polymer responsive to the change of at least one external condition (i.e. the "responsive polymer") is a thermoresponsive polymer, as defined further above, and the external condition is temperature.

In a preferred embodiment of the method according to the present invention, the suspension sample is a whole blood sample, the liquid phase of said whole blood sample is blood plasma, and the solid phase of said whole blood sample is or comprises blood cells of the whole blood sample. In a preferred embodiment, the solid phase of said whole blood sample is or comprises the majority of all blood cells, even more preferably all blood cells of the whole blood sample.

In yet a further aspect, the present invention also relates to the use of a device according to the present invention, as defined above, or of a polymer responsive to the change of at least one external condition, e.g. pH, temperature, solid conditions, presence or absence of chemicals, as defined further above, for fractionating a suspension sample into a liquid phase and a solid phase, preferably for fractionating a whole blood sample into blood plasma and blood cells, wherein, preferably, the use comprises steps a)-c), as defined further above, and optionally, step d) as also defined further above.

Without wishing to be bound by any theory, the present inventors have found that the use of responsive polymers which form a porous polymeric scaffold and an interstitial pore space within said porous polymeric scaffold, which together, make up a polymeric matrix element, allows efficient fractionation of a suspension sample into a liquid phase and a solid phase. This is particularly so in cases where suspension sample volumes are small, i.e. <1 ml. In preferred embodiments according to the present invention, the sample size used is well below 1 ml, e.g. <200 µl, preferably <150 µl. For example, in one embodiment, a typical blood sample that is used in accordance with the present invention is a sample obtained by means of a capillary, and the volume of such sample typically does not exceed 140 µl (i.e. <140 µl), and from such sample, the typical amount of plasma is <80 µl. The device according to the present invention is extremely easy to use and can be readily adapted to different suspension sample types. A particularly preferred suspension sample type is whole blood, and the device according to the present invention allows for the processing of a plurality of samples within a short period of time, due to the preferred disposability of the individual polymeric matrix element used within certain embodiments of said device which disposable polymeric matrix element is detachable or removable from the device. It is also possible that one device for fractionating a suspension sample in accordance with the present invention, may comprise more than one polymeric matrix element, e.g. 2, 3, 4, 5, 6, 10, 20, 30, 40, 50, . . . , 100, 10.000, etc. polymeric matrix elements.

The device may be a hand-held device or may be configured as a bench-top-device or as a large-scale work station-type device allowing the processing of numerous samples at the same time. In the latter case, the device may additionally be configured to comprise appropriate control units, robotic arms, to effect movement of the respective polymeric matrix element(s) and appropriate electronic control circuitry to coordinate the addition of sample, the adaptation of external conditions, such as temperature to effect an uptake of a liquid phase into the polymeric matrix element(s), the removal of said polymeric matrix element(s) from said sample(s) and a control unit capable of effecting a change of external conditions, e.g. temperature, in order to switch the polymeric matrix element(s) between an expanded state and a contracted state.

Furthermore, the present invention is illustrated by the figures, wherein

FIG. 1 shows one embodiment of a device according to the present invention comprising a polymeric matrix element contained within a sample container which is used to fractionate a blood sample.

FIG. 2 (A)-C)) shows photographs of a fractionation performed in accordance with the principles shown in FIG. 1, and (D) the results of a cell count analysis performed with samples fractionated in accordance with the present invention.

FIG. 3 shows another embodiment of a device according to the present invention wherein a polymeric matrix element is immobilized on a carrier tool which is configured to be detachably connected to heating and/or cooling means.

FIG. 4 shows an embodiment of a carrier tool with a polymeric matrix element immobilized on surface of carrier tool;

FIG. 5 shows a prototype of an embodiment of a hand-held instrument including heating and/or cooling means (A)-exploded view, and B)=assembled device), and (C) an embodiment of a device for fractionation, including a disposable carrier tool with immobilized polymeric matrix element and heating and/or cooling means in accordance with the present invention.

FIG. 6 (A)-F)) shows the results of a plasma separation process for a whole blood sample using a plasma separation device, as exemplified in FIG. 5.

Figure 7:
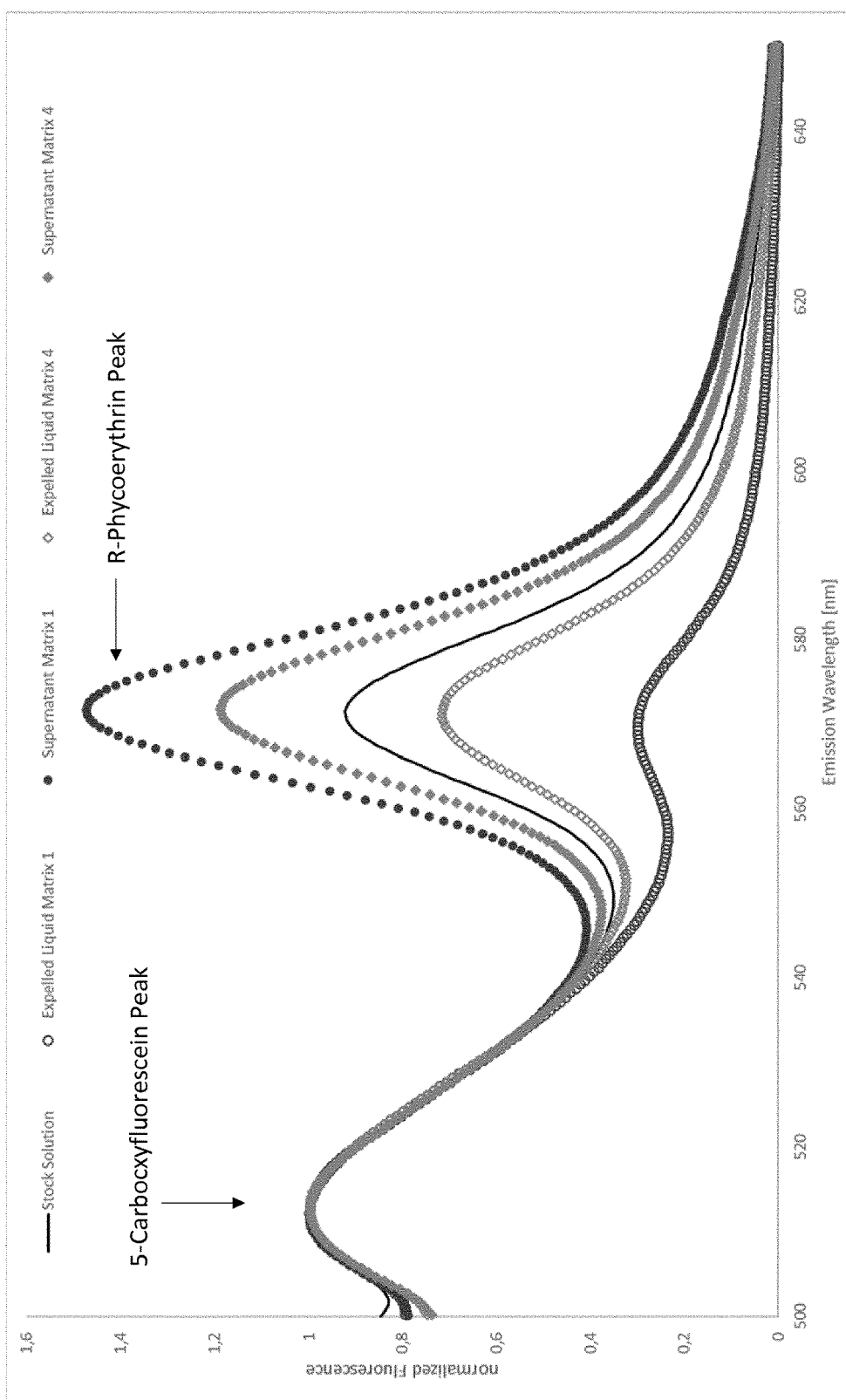

FIG. 7 shows fluorescence emission spectra of a stock solution of carboxy-fluorescein and R-phycoerythrin (R-PE), of the same stock solution after having been exposed to two different polymeric matrix elements at room temperature (during which exposure part of the stock solution will be able to enter the interstitial pore space of said polymeric matrix element), and of liquid expelled from the two different polymeric matrix elements after these have been heated to 40° C.

More specifically, FIG. 1 shows a sample container with a polymeric matrix element which is in a dry state. After addition of the sample to the sample container, the polymeric matrix element is wetted, and liquid is taken up by the polymeric matrix element, whereas the solid phase within the sample remains outside of the polymeric matrix element. Upon contact with the liquid, the polymeric matrix element swells considerably and enlarges its volume by a factor of approximately 10x. The remaining sample which is not incorporated into the polymeric matrix element is a more or less solid phase or an enriched sample of the suspended members, for example cells. In contrast thereto, the polymeric matrix element itself contains the liquid phase of said sample without the excluded suspended solid members. In the case of a blood sample, the incorporated liquid phase would be blood plasma. Depending on the size of the pores within the polymeric matrix element, this may be plasma with or without platelets. In a further step, the phase with the enriched solid phase may be removed from the sample container, or the liquid phase may be removed by removing the polymeric matrix element from the sample container. Subsequently, the polymeric matrix element is exposed to conditions in which the polymer contracts again, thus reducing the pore size of the polymeric matrix element and thus displacing the liquid from the polymeric matrix element. For example, if the polymer is a LCST polymer, such contraction can be achieved by increasing the temperature to a temperature above the LCST. The thus released liquid phase, e.g. the released plasma may be collected from the container.

Figure 2:
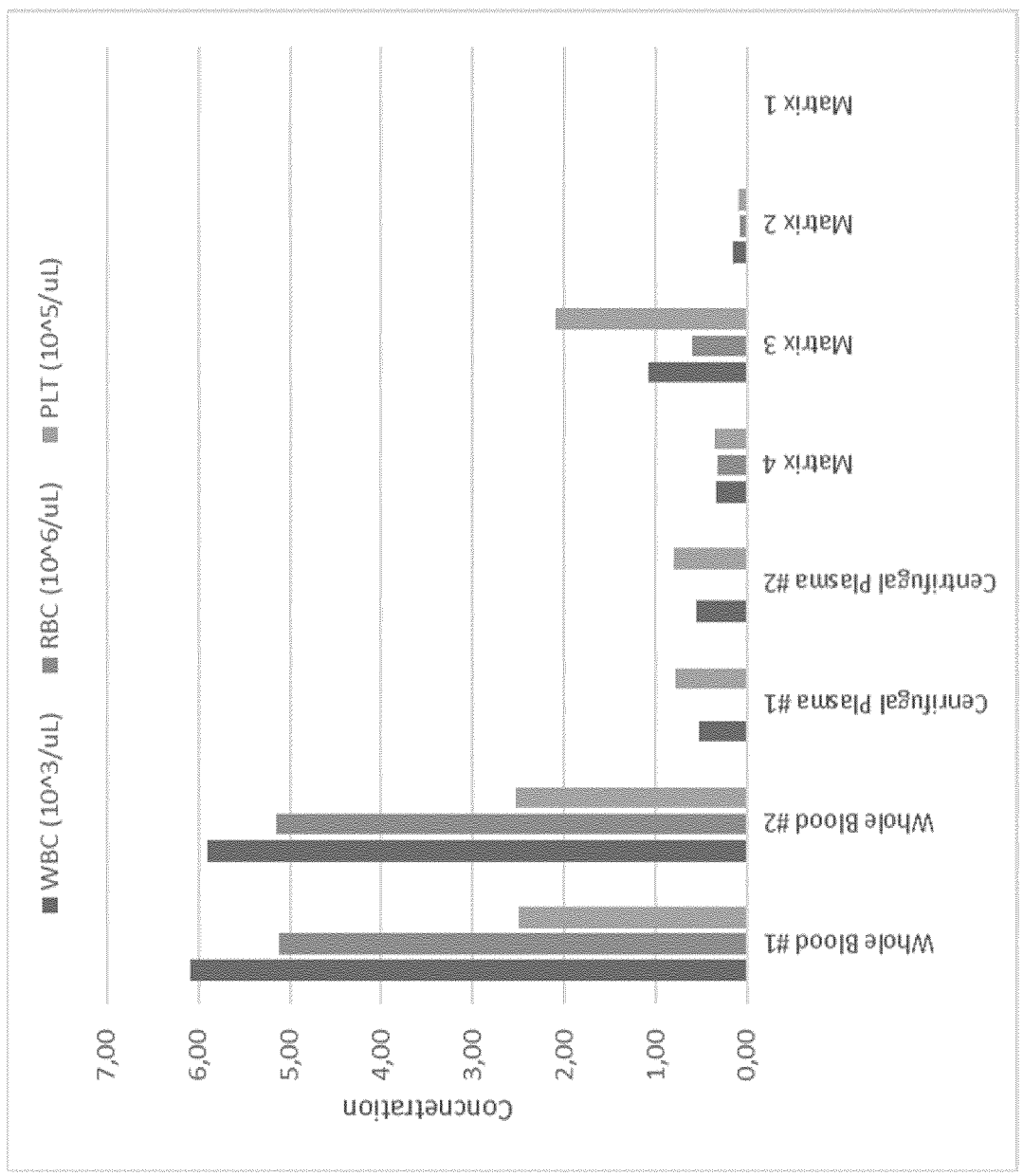

FIG. 2 shows the results of a fractionation performed in accordance with the principles outlined for FIG. 1. More specifically, 4 different polymeric matrix elements were produced as macroscopic solitary particles and were exposed to whole blood (A), and after a defined incubation removed therefrom and placed into separate further containers (B). They were then exposed to conditions allowing the release of liquid phase (plasma) from said polymeric matrix element (C). FIG. 2 D) shows the results of a cell count analysis of different samples treated in FIGS. 2A)-C) and of whole blood and of centrifugal plasma.

FIG. 3 shows another embodiment of a device in accordance with the present invention and its use. In this embodiment, a sample container containing a suspension sample is provided, and a polymer matrix element which is attached to a carrier tool is introduced into the suspension sample. The carrier tool is preferably heat conducting, and thus, the temperature to which the polymeric matrix element is exposed, can be easily changed by coupling the carrier tool to a heating and/or cooling means. Upon contact of the polymeric matrix element with the suspension sample, the polymeric matrix element takes up the liquid and excludes the suspended solid phase, e.g. cells. Again, taking blood as an example, plasma will be collected within the polymeric matrix element, until the capacity of the pores within the interstitial pore space is reached. Subsequently, the polymeric matrix element is then removed from the sample container and is transferred to a further container, i.e. a container for collecting a liquid phase (herein also sometimes referred to as "liquid phase collection container"), where again, the external conditions are changed so as to shift the polymeric matrix element from an expanded state to a contracted state, thus releasing the liquid incorporated in the polymeric matrix element. If the responsive polymer of the polymeric matrix element is a LCST polymer the change of external conditions will be an increase of the temperature above the LCST.

FIG. 4 shows an embodiment of a carrier tool with a polymeric matrix element immobilised on the surface of said carrier tool, in accordance with the present invention;

FIG. 5 shows an embodiment of a hand-held instrument that forms part of the device according to the present invention, including heating and/or cooling means, in this case a heating rod, which is configured to connect with a polymeric matrix element immobilized on a disposable carrier tool. Panel A shows an exploded view of the hand-held instrument, panel B shows the hand-held instrument in assembled form; panel C) shows an embodiment of a device for fractionation according to the present invention, including a disposable carrier tool with immobilized polymeric matrix element and heating and/or cooling means (here: heating rod);

FIG. 6 shows the results of a plasma separation process using a plasma separation device, as exemplified in FIG. 5, with the panels A)-F) showing the different stages of the separation process: Panel A) shows an embodiment of a sample container containing whole blood; panel B) shows the disposable carrier tool (as shown in FIG. 4) with a polymeric matrix element immobilized thereon inserted into said sample container; panel C) shows the hand-held instrument of FIG. 5 being connected with said disposable carrier tool by way of said heating and/or cooling means (heating rod); panel D) shows the combination of said hand-held instrument of FIG. 5 with said disposable carrier tool, after it has been withdrawn from said sample container; panel e) shows the combination of said hand-held instrument of FIG. 5 with said disposable carrier tool after it has been inserted into a new container ("a liquid phase collection container"); and panel F) shows both the (first) sample container and the liquid phase collection container after said combination of said hand-held instrument of FIG. 5 with said disposable carrier tool has been withdrawn therefrom.

FIG. 7 shows fluorescence emission spectra of a stock solution of carboxy-fluorescein and R-phycoerythrin (R-PE), of the same stock solution after having been exposed to two different polymeric matrix elements at room temperature (during which exposure part of the stock solution will be able to enter the interstitial pore space of said polymeric matrix element), and of liquid expelled from the two different polymeric matrix elements after these have been heated to 40° C. A depletion of R-Phycoerythrin from the liquid that enters the polymeric matrix elements (and a corresponding enrichment in the liquid that cannot enter the polymeric matrix element, "supernatant") can be seen.

Furthermore, reference is made to the following examples which are given to illustrate, not to limit the present invention.

EXAMPLES

Example 1

Embodiment Describing Preparation of Polymeric Matrix Element within a Sample Container and its Application for Plasma Separation Four different formulations of LCST polymer matrix have been prepared and accommodated in a sample container.

The applied protocol was as following. First a solution containing the N-Isopropylacrylamide (NIPAM) and N,N'-Methylenebisacrylamide (BIS) monomers and Ammoniumpersulfate (APS) was prepared (Premix NBA).

|  | Premix NBA |
| --- | --- |
| 20% NIPAM | 2618.6 µl |
| 2% BIS | 448 µl |
| 5% APS | 800 µl |

In order to assess the impact for different additives to the formulation the following variants were prepared:

|  | Matrix 1 | Matrix 2 | Matrix 3 | Matrix 4 |
| --- | --- | --- | --- | --- |
| Premix NBA | 870 µl | 870 µl | 870 µl | 870 µl |
| 20% PEG methyl ether acrylate, average Mn 2000 | 60 µl | 0 µl | 0 µl | 0 µl |
| 20% PEG methyl ether acrylate average Mn 480 | 0 µl | 60 µl | 306 ul | 0 µl |
| ddWater | 246 µl | 246 µl | 0 µl | 306 µl |

Plugs (i.e. "macroscopic solitary particles") of approximately 100 µL were thus formed in 0.5 mL micro reaction vials by mixing the liquid with 2 µL of 5% TEMED (degassed) under Argon. Afterwards, polymerization was allowed to occur for 30 minutes at room temperature.

The vials have been placed on a heat block at a temperature of 50° C. . . . Shrinking of the polymer could be readily observed. The expelled liquid has been collected with a micropipette and discarded. The plugs have been taken out of the micro reaction vials and transferred to 2 ml reaction tubes. 500 µl of PBS buffer were added to the tubes followed by an incubation at 20° C. for 1 hour to reswell the polymer. The PBS in excess was remover and the tubes were incubated at 60° C. for 15 min to allow the polymers to shrink. The expelled liquid was discarded. This washing procedure was repeated once more.

Samples of 150 µL of whole blood freshly collected in EDTA coated vacutainer tubes have been added to the respective vials containing the shrunken polymer as shown in FIG. 2A), and left for 30 minutes at room temperature.

After 30 minutes the sample was removed from the vials with the swollen plugs. FIG. 2B) shows the four vials with the plugs. It is apparent that the different matrices have taken up different amounts of liquid. Moreover, different amounts of whole blood have stuck to the plugs depending on their formulation.

The vials with the plugs have then been placed on a heating block for one minute at 40° C. The polymer contracted and liquid was expelled from the matrix material. The expelled liquid has been collected in separate vials. As shown in FIG. 2C), different amounts of liquid have been expelled at the defined temperature, also different levels of coloring of the sample due to trapped whole blood can be seen.

The collected samples have been analyzed on a laboratory hematology analyzer (Sysmex) and data have been compared against the cell counts ("WBC"=white blood cells; "RBC"=red blood cells; and "PLT"=platelets) obtained with whole blood and plasma generated by centrifuging a sample of 250 µl at 1.500 g for 1 minute. Data for two aliquots of one sample of whole blood ("Whole Blood #1" and "Whole Blood #2"), two plasma samples generated by centrifugation from the same sample of whole blood ("Centrifugal Plasma #1" and "Centrifugal Plasma #2") and data for liquid collected from the different formulation of the LCST polymer matrices ("Matrix 1", "Matrix 2", "Matrix 3", "Matrix 4") are summarized in FIG. 2D).

The separating effect achieved by the application of the matrix is clearly visible. Moreover a simple approach to optimizing the separating effect by adding different reagents to the polymer preparation is shown. It appears that matrices 1 and 2 are the most efficient ones in separating blood cells from the liquid components of the blood sample.

Example 2

Polymeric Matrix Element Immobilized on a Substrate

An aluminum shell has been designed as a part of a disposable for plasma separation. The aluminum shell functions as carrier tool acting as a substrate having a surface on which a polymeric matrix element is immobilized. The shell surface has been roughened with sandpaper to make a polymeric matrix element better adhere to the surface.

A formulation of a LCST polymer matrix as polymeric matrix element has been prepared as follows: First, a solution containing N-Isopropylacrylamide (NIPAM) and N,N'-Methylenebisacrylamide (BIS) monomers and Ammoniumpersulfate (APS) was prepared (Premix NBA).

|  | Premix NBA |
| --- | --- |
| 20% NIPAM | 655 µl |
| 2% BIS | 112 µl |
| 5% APS | 200 µl |

To this mix a PEG methyl ether acrylate and water was added as follows:

|  | LCST-Mix |
| --- | --- |
| Premix NBA | 870 µl |
| 20% PEG methyl ether acrylate average Mn 480 | 120 µl |
| ddWater | 186 µl |

194 µl aliquots of this solution was added to Sarsted Microvette sampling vessels. The solution in the vessels has been degassed and saturated with Argon in 4 push pull cycles.

These aliquots were mixed with 4 µl of 5% TEMED (degassed) under Argon and the aluminum shell was dipped into the solution. Following an incubation time of 30 minutes the aluminum shell has been contacted to a heat source and the polymer contracted on the shell. The shell with the polymer has been removed from the vial and transferred into a new vial containing PBS washing buffer. The polymer was allowed to reswell in the washing buffer for one hour. This washing step has been repeated two times.

This disposable device is shown in FIG. 4 and is subsequently used as a carrier tool according to the exemplary process described in Example 3.

Example 3

Description of Prototype as Developed by Blink AG

As a possible product based on the invention, a handheld separation device has been developed. Such a product may be particularly useful in the context of enabling diagnostics applications at the point-of-care. Many diagnostic tests require plasma as the sample matrix. However, in many settings no adequate means are available for generating plasma from whole blood, in particular from capillary blood samples that otherwise can be easily obtained by common fingerstick sampling techniques. Here we describe a pen-like hand-held battery-operated instrument in combination with a disposable device.

The instrument consists of the basic modules shown in FIGS. 5A) (exploded view) and 5B) (assembled device) which is to be used in conjunction with a disposable carrier tool as shown in FIG. 4. The combination of the hand-held device of FIGS. 5A) and B) with a disposable carrier tool is an embodiment of a device configured for fractionation in accordance with the present invention and is shown in FIG. 5C)

The hand-held instrument of FIGS. 5A) and 5B) is designed to heat a metal rod to a predefined temperature (above the LCST of the filter polymer). The control circuit is accommodated on a separate electronics board containing a power management circuit connected to an AA battery accommodated within the instrument body, a LED for reporting the status of the device as well as a button for activating the device. The control circuit is connected to a heating rod (("heating and/or cooling means") with dimensions allowing it to be combined with and introduced into a special "disposable carrier tool" (as e.g. shown in FIG. 4) with a LCST-polymer coating acting as a polymeric matrix element immobilized on a surface of said carrier tool.

The "disposable carrier tool"-device comprises a plastic part equipped with a pit to accommodate tightly the heating rod of the device. On its outer face the disposable carrier tool is coated with the LCST polymer as outlined in example 2 and shown in FIG. 4.

The disposable carrier tool is designed to fit into a sample container, e.g. a standard Microvette sample container containing a required amount, e.g. 100 µL, of collected whole blood. Upon introduction of the disposable carrier tool into the sample container the plasma wets the polymer and occupies its inner space whereas any particular materials contained in the sample remain outside of the polymer matrix. After a sufficient incubation time the disposable carrier tool is brought into contact with the hand-held instrument of FIGS. 5A) and 5B) and the heating and/or cooling means thereof, i.e. the heating rod, by introducing the heating rod of the instrument into the pit of the disposable carrier tool. By firmly pressing the rod into the disposable carrier tool, the latter is attached to the former. Then the instrument with the disposable carrier tool attached is removed from the sample container, and the disposable carrier tool is introduced into another container, i.e. an empty container ("a liquid phase collection container").

Upon pushing the button, the hand-held instrument is activated. A green (or any other suitable color) LED flashes until a predefined temperature above the LCST has been reached. The LED now lights up permanently in green. The polymer shrinks in the disposable carrier tool and releases the trapped plasma into the liquid phase collection container. The disposable carrier tool is withdrawn from the liquid phase collection container, removed from the hand-held instrument of FIGS. 5A and 5B and safely discarded. The hand-held instrument can now be used for a new separation task. The device is switched off by once pressing the button. Any malfunctions are indicated by a red light.

The whole workflow is shown in FIGS. 6A)-F), wherein FIG. 6A) shows a standard sample container containing a suspension sample, in this case whole blood; FIG. 6B) shows the disposable carrier tool of FIG. 4 (with a polymeric matrix element immobilised thereon) inserted into said sample container such that the polymeric matrix element gets exposed to said suspension sample, i.e. in this case to said whole blood; FIG. 6C) shows the disposable carrier tool connected with the heating and/or cooling means (in this case the heating rod) of the hand-held device of FIG. 5); FIG. 6D) shows the combination of the disposable carrier tool and hand-held device having been withdrawn from the sample container after it had been exposed to said suspension sample for a defined period of time and after the liquid phase had been bound by or incorporated into said polymeric matrix element; FIG. 6E) shows the same combination (of the disposable carrier tool and hand-held device) being introduced into a further, empty container, i.e. a liquid phase collection container, where the heating and/or cooling means, in this case the heating rod, is operated to heat above the LCST of said polymeric matrix element, thereby releasing the liquid phase bound by said polymeric matrix element, into said liquid phase collection container; FIG. 6E) (on the left side) shows the (first) sample container where the whole blood had been originally kept in and exposed to said polymeric matrix element and (on the right side) the (further) liquid phase collection container into which the liquid phase has been released after the heating rod has been heated above the LCST of the polymeric matrix element.

Example 4

Enrichment and Depletion of Soluble Fluorescent Compounds of Different Size

The invented methodology has been applied for the enrichment of soluble molecules in a solution in a small volume of a liquid.

Polymer plugs (i.e. "polymeric matrix elements") prepared according to the methodology described in Example #1 have been used for changing the composition of a stock solution containing 1,62 µmol/L of the small organic dye 5-Carboxyfluorescein (M=376.32 g/mol; C0537 SIGMA-ALDRICH) ("5CF") and 0,4 nmol/L of the macromolecular fluorescent protein R-Phycoerythrin (M=250 kDa, Thermo Fisher P801) ("R-PE"). The fluorescent spectrum of the stock solution has been collected using a Lambda 50 Fluorescence Spectrometer (Perkin Elmer). The spectrum is shown in black with a solid line in FIG. 7, with an emission peak for R-PE at @570 nm.

Two different plugs of LCST polymer matrix prepared as outlined in Example #1 made up of PNIPAM/PEG Acrylate and PNIPAM have been used to investigate the effect of the matrix on the composition of the liquid. The vials containing the plugs have been placed in a heat block at 40° C. for one minute. The expelled liquid has been collected with a micropipette and discarded. 150 μL of the stock solution containing 5-Carboxyfluorescein and R-Phycoerythrin has been added to vials and left at room temperature for 5 minutes. Thereafter the supernatants have been collected and fluorescent spectra obtained for both samples ("Supernatant"). The vials with the plugs have been placed in a heat block at 40° C. for one minute and the expelled liquid collected with a micropipette. Fluorescent spectra have been obtained for the expelled liquid samples ("matrix 1" (empty circles), and "matrix 4" (empty diamonds), respectively) and compared against the spectra for the stock solution (marked black, solid line) and against the supernatants (Matrix 1, filled circles, and matrix 4, filled diamonds. Normalized spectra for the two different matrix preparations and the stock solution are shown in FIG. 7. It can be seen that both polymeric matrix elements are capable of enriching R-Phycoerythrin in the respective supernatant (FIG. 7: "Supernatant Matrix 1", filled circles, and "Supernatant Matrix 4", filled diamonds) by excluding the R-Phycoerythrin from the interstitial pore space of the polymeric matrix element and thereby depleting it from the liquid that enters the interstitial pore space of the polymeric matrix element and that it is subsequently released again when the polymeric matrix element is heated above its LCST (FIG. 7: "Expelled Liquid Matrix 1", empty circles, and "Expelled Liquid Matrix 4", empty diamonds). Hence, the polymeric matrix elements according to the present invention can be successfully used to separate two dissolved components of different molecular weights, and/or to enrich/deplete them respectively. It is also evident from the data that the different matrix preparations show different capacities to enrich or deplete certain reagents from a solution.

REFERENCES

1. Tuck, M. K., et al., *Standard operating procedures for serum and plasma collection: early detection research network consensus statement standard operating procedure integration working group.* J Proteome Res, 2009. 8(1): p. 113-7.
2. Smith, W. C., *Improved method for separating the cellular components of blood samples.* 1989, Google Patents.
3. Pall David B, R.E.N.Y.U.S., et al., *Device and method for blood separation.|Vorrichtung und Verfahren zur Trennung von Blut.|Dispositif et méthode pour la séparation du sang. |Device and method for blood separation|Dispositif et méthode pour la séparation du sang |Vorrichtung und Verfahren zur Trennung von Blut*, G.C.N.Y.U.S. Pall Corporation, Editor. 1991: EP.
4. Liu, C., et al., *Membrane-based, sedimentation-assisted plasma separator for point-of-care applications.* Analytical chemistry, 2013. 85(21): p. 10463-10470.
5. Nakayama, K. and K. Morimoto, *Assessment of accuracy of immediate blood separation method: a novel blood analysis strategy.* Environ Health Prev Med, 2011. 16(1): p. 1-5.
6. Hagihara Takeaki, O.s.O.k.J.P. and O.s.O.k.J.P. Aoki Satoshi, *A compact plasma separator and an apparatus containing the same.|Kompakter Plasmaseparator und Vorrichtung mit einemsolchen Separator.|Séparateur compact de plasma et dispositif contenant un tel séparateur.|A compact plasma separator and an apparatus containing the same|Séparateur compact de plasma et dispositif contenant un tel séparateur|Kompakter Plasmaseparator und Vorrichtung mit einem solchen Separator*, C.K.T.J.P. Asahi Medical Co. Ltd, Editor. 1993: EP.
7. McNeely Michael Ryan, U.S., *AUTOMATIC PLASMA SEPARATION AND METERING|SÉPARATION ET DOSAGE AUTOMATIQUES DU PLASMA*, U.S.M.M.R.U.S. McNeely Michael Ryan, Editor. 2017: WO.
8. Rueda Ivan, P.C.A.U.S., et al., *PROCESSING BLOOD SAMPLES TO DETECT TARGET NUCLEIC ACIDS*, C.C.A.U.S.M.I.N.C.U.S.M.I.N.C. Monolythix Inc, Editor. 2017: US.
9. Mukherjee, S., et al., *Plasma separation from blood: the 'lab-on-a-chip' approach.* Crit Rev Biomed Eng, 2009. 37(6): p. 517-29.
10. Gandhi, A., et al., *Studies on thermoresponsive polymers: Phase behaviour, drug delivery and biomedical applications.* Asian Journal of Pharmaceutical Sciences, 2015. 10(2): p. 99-107.
11. Constantinou, A. P. and T. K. Georgiou, *Tuning the gelation of thermoresponsive gels.* European Polymer Journal, 2016. 78 (Supplement C): p. 366-375.
12. de la Rosa, V. R., P. Woisel, and R. Hoogenboom, *Supramolecular control over thermoresponsive polymers.* Materials Today, 2016. 19(1): p. 44-55.

The invention claimed is:

1. A device configured for fractionating a suspension sample into a liquid phase and a solid phase, said device comprising at least one polymeric matrix element,
    said at least one polymeric matrix element comprising a porous polymeric scaffold and an interstitial pore space within said polymeric scaffold, said intestinal pore space having pores the diameter of which is <5 μm;
    wherein said porous polymeric scaffold is composed of a polymer responsive to a change of temperature to which said polymeric matrix element, during use of said device, is exposed;
    wherein said at least one polymeric matrix element, due to the presence of said responsive polymer, has the capability of reversibly adopting an expanded and a contracted state,
    wherein said device further comprises means to effect a change of temperature to which said polymeric matrix element, during use of said device, is exposed, wherein said means are heating and/or cooling means that are part of said device and/or are integrated in said device; and
    wherein said polymer responsive to a change of temperature is a thermoresponsive polymer having a lower critical solution temperature (LCST polymer) or a thermoresponsive polymer having an upper critical solution temperature (UCST polymer).

2. The device according to claim 1, further comprising at least one sample container, said at least one sample container containing, or being configured to contain, said at least one polymeric matrix element, said at least one sample container being capable of receiving-a a suspension sample.

3. The device according to claim 1, wherein said at least one polymeric matrix element is either a macroscopic solitary particle or said at least one polymeric matrix element is a macroscopic body or layer immobilized on a surface of a substrate within said device.

4. The device according to claim 1, wherein said at least one polymeric matrix element is detachable or removable from said device.

5. The device according to claim 1, wherein said heating and/or cooling means are configured to come into contact with said suspension sample or to become connected with said suspension sample.

6. The device according to claim 1, wherein said device further comprises a carrier tool configured to allow the handling of said at least one polymeric matrix element, said carrier tool acting as a substrate having a surface on which said at least one polymeric matrix element is immobilized, said carrier tool being dimensioned such as to be able to be dipped into a suspension sample, and such as to be able to bring said at least one polymeric matrix element into contact with said suspension sample.

7. The device according to claim 6, wherein said carrier tool is configured to be able to effect a change of temperature to which said polymeric matrix element, during use of said device, is exposed.

8. The device according to claim 7, wherein said carrier tool comprises heating and/or cooling means for heating and/or cooling said at least one polymeric matrix element, or said carrier tool is connected to or contacted with heating and/or cooling means for heating and/or cooling said at least one polymeric matrix element.

9. The device according to claim 6, wherein said carrier tool is a disposable single-use carrier tool and is configured to be detachably connected to, detachably contacted with or to detachably comprise said heating and/or cooling means.

10. The device according to claim 1, wherein said device further comprises at least one liquid phase collection container, said at least one liquid phase collection container being configured to take up said polymeric matrix element and/or a carrier tool, if present, with said polymeric matrix element being immobilized on said carrier tool.

11. The device according to claim 2, wherein a) said sample container and/or a carrier tool, if present, and/or a liquid phase collection container, if present, comprise means to mechanically remove said solid phase from said polymeric matrix element; or b) said sample container and/or a carrier tool, if present, and/or a liquid phase collection container, if present, comprise a material having an affinity to said solid phase to which material said solid phase adheres, when being or getting in contact with it; or c) said sample container and/or a carrier tool, if present, and/or a liquid phase collection container, if present, comprise means to wash off said solid phase from said polymeric matrix element; or d) wherein said device further comprises a separate tool to remove said solid phase from said polymeric matrix element.

12. The device according to claim 1, wherein said suspension sample is a whole blood sample, said liquid phase of said whole blood sample is blood plasma, and said solid phase of said whole blood sample is, or comprises, blood cells of said whole blood sample.

13. The device according to claim 1, wherein said polymer responsive to the change of at least one external condition to which said thermoresponsive polymer having a lower critical solution temperature (LCST polymer) is selected from poly(N-isopropylacrylamide) (pNIPAM), poly(N-isopropylacrylamide/N,N'-Methylenebis(acrylamide), poly(N-isopropylacrylamide)-co-(acrylic acid), poly(N-isopropylacrylamide)-co-(acrylic acid)-co-(poly(ethyleneglycol) methyl ether acrylate, poly(N-isopropylacrylamide)-co-(poly(ethyleneglycol) diacrylate, poly(N-isopropylacrylamide)-co-(poly(ethyleneglycol) methyl ether acrylate, poly [2-(dimethylamino)ethyl methacrylate] (pDMAEMA), hydroxypropylcellulose, poly(vinylcaprolactame) (P(VCL), and polyvinyl methyl ether; and said thermoresponsive polymer having an upper critical solution temperature (UCST) is selected from poly(N-acryloyl glycinamide) (PNAGA), poly(allylamine)-co-poly (allylurea) and its derivatives, poly (methacrylamide), poly(N-acryloylaspargineamide), poly(N-methacryloylglutamineamide), poly(acrylamide)-co-(acrylonitrile), poly(sulfobetaine) s, and poly (phosphorylcholine) s.

14. The device according to claim 1, wherein said interstitial pore space has pores the average diameter of which is <3 µm.

15. The device according to claim 1, wherein said device is dimensioned such as to fractionate a suspension sample having a volume in the range of from 10 µl to 500 µl, and wherein the interstitial pore space has a volume which takes up at least 50% of said suspension sample.

16. A method of fractionating a suspension sample into a liquid phase and a solid phase, said method comprising the steps:
a) providing, in any order, but separately from each other, a device according to claim 1, and a suspension sample, wherein said at least one polymeric matrix element of said device is in dry state, or wherein said at least one polymeric matrix element of said device is provided under conditions in which said responsive polymer is in a contracted state but wherein said at least one polymeric matrix element of said device is in a moist state;
b) exposing said at least one polymeric matrix element of said device to said suspension sample to a temperature allowing said polymeric matrix element to reversibly adopt an expanded state and thus allowing a liquid phase in said suspension sample to enter said interstitial pore space of said at least one polymeric matrix element, whilst excluding a solid phase in said suspension sample from said interstitial pore space;
c) removing said at least one polymeric matrix element from said sample, thereby removing said liquid phase contained within said interstitial pore space from said sample and thereby separating said liquid phase from a solid phase in said sample; and
d) changing the temperature to which said polymeric matrix element is exposed, to a temperature allowing said polymeric matrix element to reversibly adopt a contracted state, thereby releasing said liquid phase from said polymeric matrix element.

17. The method according to claim 16, wherein, in step c), said at least one polymeric matrix element is removed from a sample container and is transferred to a liquid phase collection container.

18. A method for fractionating a whole blood sample into blood plasma and blood cells, wherein said method comprises
(a) providing, in any order, but separately from each other, a device according to claim 1, and the whole blood sample, wherein said at least one polymeric matrix element of said device is in dry state, or wherein said at least one polymeric matrix element of said device is provided under conditions in which said responsive polymer is in a contracted state but wherein said at least one polymeric matrix element of said device is in a moist state;
(b) exposing said at least one polymeric matrix element of said device to said whole blood sample to a temperature allowing said polymeric matrix element to reversibly adopt an expanded state and thus allowing blood plasma in said whole blood sample to enter said interstitial pore space of said at least one polymeric matrix element, whilst excluding blood cells in said whole blood sample from said interstitial pore space;
(c) removing said at least one polymeric matrix element from said sample, thereby removing said blood plasma contained within said interstitial pore space from said sample and thereby separating said blood plasma from blood cells in said sample; and (d) changing the temperature to which said polymeric matrix element is exposed, to a temperature allowing said polymeric matrix element to reversibly adopt a contracted state, thereby releasing said blood plasma from said polymeric matrix element.

* * * * *